(12) United States Patent
Browning et al.

(10) Patent No.: US 8,455,445 B2
(45) Date of Patent: *Jun. 4, 2013

(54) METHODS FOR INHIBITING LYMPHOTOXIN-β RECEPTOR SIGNALING IN TH1 CELL-ASSOCIATED DISORDERS

(75) Inventors: Jeffrey L. Browning, Brookline, MA (US); Christopher D. Benjamin, Beverly, MA (US); Paula S. Hochman, Newton, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/037,092

(22) Filed: Feb. 28, 2011

(65) Prior Publication Data

US 2011/0250200 A1 Oct. 13, 2011

Related U.S. Application Data

(60) Continuation of application No. 11/982,415, filed on Oct. 31, 2007, now Pat. No. 7,951,371, which is a continuation of application No. 10/077,406, filed on Feb. 15, 2002, now Pat. No. 7,427,403, which is a division of application No. 09/000,166, filed as application No. PCT/US96/12010 on Jul. 19, 1996, now Pat. No. 6,403,087, which is a continuation-in-part of application No. 08/505,606, filed on Jul. 21, 1995, now Pat. No. 5,925,351.

(51) Int. Cl.
*A61K 38/16* (2006.01)
*A61P 19/02* (2006.01)
*C07K 19/00* (2006.01)
*C07K 14/715* (2006.01)

(52) U.S. Cl.
USPC ........ 514/21.2; 514/16.6; 514/20.8; 514/885; 530/351; 530/387.3; 435/69.1; 424/134.1; 930/143

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,338,397 A | 7/1982 | Gilbert et al. | |
| 4,485,045 A | 11/1984 | Regen | |
| 4,544,545 A | 10/1985 | Ryan et al. | |
| 4,758,549 A | 7/1988 | Mitsuhashi et al. | |
| 4,816,567 A | 3/1989 | Cabilly et al. | |
| 4,822,605 A | 4/1989 | Powell | |
| 4,849,509 A | 7/1989 | Thurin et al. | |
| 4,959,457 A | 9/1990 | Bringman | |
| 5,082,783 A | 1/1992 | Ernst et al. | |
| 5,225,538 A | 7/1993 | Capon et al. | |
| 5,661,004 A | 8/1997 | Browning et al. | |
| 5,670,149 A | 9/1997 | Browning et al. | |
| 5,795,964 A | 8/1998 | Browning et al. | |
| 5,925,351 A | 7/1999 | Browning et al. | |
| 6,312,691 B1 | 11/2001 | Browning et al. | |
| 6,403,087 B1 | 6/2002 | Browning et al. | |
| 6,669,941 B1 | 12/2003 | Browning et al. | |
| 7,001,598 B2 | 2/2006 | Browning et al. | |
| 7,030,080 B2 | 4/2006 | Browning et al. | |
| 7,060,667 B1 | 6/2006 | Browning et al. | |
| 7,255,854 B1 | 8/2007 | Browning et al. | |
| 7,309,492 B2 | 12/2007 | Browning et al. | |
| 7,427,403 B2 | 9/2008 | Browning et al. | |
| 7,452,530 B2 | 11/2008 | Browning et al. | |
| 7,459,537 B2 | 12/2008 | Browning et al. | |
| 7,951,371 B2 * | 5/2011 | Browning et al. | 424/134.1 |
| 2002/0001585 A1 | 1/2002 | Browning et al. | |
| 2002/0039580 A1 | 4/2002 | Browning et al. | |
| 2002/0197254 A1 | 12/2002 | Browning et al. | |
| 2004/0058394 A1 | 3/2004 | Garber et al. | |
| 2004/0198635 A1 | 10/2004 | Browning et al. | |
| 2005/0037003 A1 | 2/2005 | Browning et al. | |
| 2005/0281811 A1 | 12/2005 | Browning et al. | |
| 2006/0104971 A1 | 5/2006 | Garber et al. | |
| 2006/0134102 A1 | 6/2006 | LePage et al. | |
| 2006/0222644 A1 | 10/2006 | Garber et al. | |
| 2006/0280722 A1 | 12/2006 | Browning et al. | |

(Continued)

FOREIGN PATENT DOCUMENTS

DE 3218121 A1 11/1983
EP 0058481 B1 8/1982

(Continued)

OTHER PUBLICATIONS

Fava et al, 2011. Arthritis Research & Therapy. 13: R182. pp. 1-20.*
Youinou et al, 2011. Arthritis Research & Therapy. 13: 227. pp. 1-10.*
Phillips, J Pharm Pharmacology 53: 1169-1174, 2001.*
Vidal et al. 2005. European Journal of Cancer. 41: 2812-2818.*
Pirollo et al, 2008. Cancer Res. 68(5): 1247-1250.*
Abe, Yasuhito et al., "Expression of Membraine-associated Lymphotoxin/Tumor Necrosis Factor-b on Human Lymphokine-activated Killer Cells," Jpn. J. Cancer Res., vol. 82:23-26 (1991).
Abe, Yasuhito et al., "Studies of Membrane-Associated and Soluble (Secreted) Lymphotoxin in Human Lymphokine-Activated T-Killer Cells in Vitro," Lymphokine and Cytokine Research, vol. 11(2):115-121 (1992).

(Continued)

*Primary Examiner* — Zachary Howard
(74) *Attorney, Agent, or Firm* — Nelson Mullins Riley & Scarborough LLP; Debra J. Milasincic, Esq.

(57) ABSTRACT

This invention relates to compositions and methods comprising "lymphotoxin-β-receptor blocking agents", which block lymphotoxin-β receptor signalling. Lymphotoxin-β receptor blocking agents are useful for treating lymphocyte-mediated immunological diseases, and more particularly, for inhibiting Th1 cell-mediated immune responses. This invention relates to soluble forms of the lymphotoxin-β receptor extracellular domain that act as lymphotoxin-β receptor blocking agents. This invention also relates to the use of antibodies directed against either the lymphotoxin-β receptor or its ligand, surface lymphotoxin, that act as lymphotoxin-β receptor blocking agents. A novel screening method for selecting soluble receptors, antibodies and other agents that block LT-β receptor signalling is provided.

16 Claims, 6 Drawing Sheets

U.S. PATENT DOCUMENTS

| | | | |
|---|---|---|---|
| 2007/0116668 | A1 | 5/2007 | Browning et al. |
| 2007/0154476 | A1 | 7/2007 | Browning et al. |
| 2008/0219967 | A1 | 9/2008 | Browning et al. |

FOREIGN PATENT DOCUMENTS

| | | |
|---|---|---|
| EP | 0367575 A1 | 5/1990 |
| EP | 0509553 B1 | 10/1992 |
| EP | 0873998 A2 | 10/1998 |
| WO | 92/00329 A1 | 1/1992 |
| WO | 94/04679 A1 | 3/1994 |
| WO | 94/13808 A2 | 6/1994 |
| WO | 96/01121 A1 | 1/1996 |
| WO | 96/22788 A1 | 8/1996 |
| WO | 96/23071 A2 | 8/1996 |
| WO | 97/03678 A1 | 2/1997 |
| WO | 97/03687 A1 | 2/1997 |
| WO | 97/04658 A1 | 2/1997 |
| WO | 98/17313 A2 | 4/1998 |
| WO | 98/18928 A1 | 5/1998 |
| WO | 2007/146414 A2 | 12/2007 |

OTHER PUBLICATIONS

Acharya, S.K. et al., "A preliminary open trial on interferon stimulator (SNMC) derived from *Glycyrrhiza glabra* in the treatment of subacute hepatic failure," Indian J. Med. Res. [B], vol. 98:69-74 (1993).

Aebersold, Ruedi H. et al., "Internal amino acid sequence analysis of proteins separated by one- or two-dimensional gel electrophoresis after in situ protease digestion on nitrocellulose," Proc. Natl. Acad. Sci. USA, vol. 84:6970-6974 (1987).

Aggarwal, Bharat B. et al., "Human Lymphotoxin," The Journal of Biological Chemistry, vol. 259(1):686-691 (1984).

Aggarwal, Bharat B. et al., "Primary Structure of Human Lymphotoxin Derived from 1788 Lymphoblastoid Cell Line," The Journal of Biological Chemistry, vol. 260(4):2334-2344 (1985).

Akashi, Makoto et al., "Lymphotoxin: Stimulation and Regulation of Colony-Stimulating Factors in Fibroblasts," Blood, vol. 74(7):2383-2390 (1989).

Alderson, Mark R. et al., "Regulation of apoptosis and T cell activation by Fas-specific mAb," International Immunology, vol. 6(11):1799-1806 (1994).

Alexopoulou, Lena et al., "Immunoregulatory Activities of Transmembrane TNF Revealed in Transgenic and Mutant Mice," 6th International TNF Congress, p. 228, No. 110 (1996).

Alimzhanov, Marat B. et al., "Abnormal development of secondary lymphoid tissues in lymphotoxin b-deficient mice," Proc. Natl. Acad. Sci. USA, vol. 94:9302-9307 (1997).

Amiri, Payman et al., "Tumour necrosis factor a restores granulomas and induces parasite egg-laying in schistosome-infected SCID mice," Nature, vol. 356:604-607 (1992).

Anderson, W. French, "Human gene therapy," Nature, vol. 392:25-30 (1998).

Andersson, Ulf et al., "Characterization of individual tumor necrosis factor a- and b-producing cells after polyclonal T cell activation," Journal of Immunological Methods, vol. 123:233-240 (1989).

Andrews, Janet S. et al., "Characterization of the Receptor for Tumor Necrosis Factor (TNF) and Lymphotoxin (LT) on Human T Lymphocytes, TNF and LT Differ in Their Receptor Binding Properties and the Induction of MHC Class I Proteins on a Human CD4+ T Cell Hybridoma," The Journal of Immunology, vol. 144(7):2582-2591 (1990).

Androlewicz, Matthew J. et al., "Lymphotoxin Is Expressed as a Hetermeric Complex with a Distinct 33-kDa Glycoprotein on the Surface of an Activated Human T Cell Hybridoma," The Journal of Biological Chemistry, vol. 267 (4):2542-2547 (1992).

Armitage, Richard J. et al., "Molecular and biological characterization of a murine ligand for CD40," Nature, vol. 357:80-82 (1992).

Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," J. Exp. Med., vol. 177:1439-1450 (1993).

Badenhoop, K. et al., "TNF-a gene polymorphisms in Type 1 (insulin-dependent) diabetes mellitus," *Diabetologia*, vol. 32:445-448 (1989).

Baens, Mathijs et al., "Construction and Evaluation of a hncDNA Library of Human 12p Transcribed Sequences Derived from a Somatic Cell Hybrid," Genomics, vol. 16:214-218 (1993).

Banks, Theresa A. et al., "Lymphotoxin-a-Deficient Mice," The Journal of Immunology, vol. 155:1685-1693 (1995).

Barnetson, "Hypersensitivity—Type IV," Mosby-Year Book Europe Ltd., Chpt. 22, pp. 22.1-22.12 (1993).

Bernstein, David I. et al., "Effects of therapy with an immunomodulator (imiquimod, R-837) alone with the acyclovir on genital HSV-2 infection in guinea-pigs when begun after lesion development," Antiviral Research, vol. 20:45-55 (1993).

Bethell, Delia B. et al., "Pathophysiologic and Prognostic Role of Cytokines in Dengue Hemorrhagic Fever," JID, vol. 177:778-782 (1998).

Beutler, B. et al., "Passive Immunization Against Cachectin/Tumor Necrosis Factor Protects Mice from Lethal Effect of Endotoxin," Science, vol. 229:869-871 (1985).

Beutler, Bruce et al., "The History, Properties, and Biological Effects of Cachectin," Biochemistry, vol. 27 (20):7575-7582 (1988).

Bowie, James U. et al., "Deciphering the Message in Protein Sequences: Tolerance to Amino Acid Substitutions," Science, vol. 247:1306-1310 (1990).

Bringman, Timothy S. et al., "Monoclonal Antibodies to Human Tumor Necrosis Factors Alpha and Beta: Application for Affinity Purification, Immunoassays, adn as Structural Probes," Hybridoma, vol. 6(5):489-507 (1987).

Briskin, Michael J. et al., "MAdCAM-1 has homology to immunoglobulin and mucin-like adhesion receptors and to IgA1," Nature, vol. 363:461-464 (1993).

Browning, Jeffrey L. et al., "Characterization of Surface Lymphotoxin Forms, Use of Specific Monoclonal Antibodies and Soluble Receptors," The Journal of Immunology, vol. 154:33-46 (1995).

Browning, Jeffrey L. et al., "Lymphotoxin and an Associated 33-kDa Glycoprotein Are Expressed on the Surface of an Activated Human T Cell Hybridoma," The Journal of Immunology, vol. 147(4):1230-1237 (1991).

Browning, Jeffrey L. et al., "Lymphotoxin b, a Novel Member of the TNF Family That Forms a Heteromeric Complex with Lymphotoxin on the Cell Surface," Cell, vol. 72:847-856 (1993).

Browning, Jeffrey L. et al., "Signaling through the Lymphotoxin b Receptor Induces the Death of Some Adenocarcinoma Tumor Lines," J. Exp. Med., vol. 183:867-878 (1996).

Browning, Jeffrey et al., "Studies on the Differing Effects of Tumor Necrosis Factor and Lymphotoxin on the Growth of Several Human Tumor Lines," The Journal of Immunology, vol. 143(6):1859-1867 (1989).

Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).

Cavender, Druie E. et al., "Endothelial Cell Activation Induced by Tumor Necrosis Factor and Lymphotoxin," American Journal of Pathology, vol. 134(3):551-560 (1989).

Cavender, Druie et al., "Pathways to chronic inflammation in rheumatoid synovitis," Federation Proceedings, vol. 46:113-117 (1987).

Cavert, Winston et al., "Kinetics of Response in Lymphoid Tissues to Antiretroviral Therapy of HIV-1 Infection," Science, vol. 276:960-964 (1997).

Chaplin, David D. et al., "Cytokine regulation of secondary lymphoid organ development," Current Opinion in Immunology, vol. 10:289-297 (1998).

Chen, Chyi-Ying A. et al., "AU-rich elements: characterization and importance in mRNA degradation," TIBS, vol. 20:465-470 (1995).

Cher, Daniel J. et al., "Two Types of Murine Helper T Cell Clone, II. Delayed-Type Hypersensitivity is Mediated by TH1 Clones," The Journal of Immunology, vol. 138(11):3688-3694 (1987).

Chisholm, Patricia L. et al., "Monoclonal antibodies to the integrin a-4 subunit inhibit the murine contact hypersensitivity response," Eur. J. Immunol., vol. 23:682-688 (1993).

Cotran, Ramzi S. et al., "Endothelial Activation, Its Role in Inflammatory and Immune Reactions," Endothelial Cell Biology in Health and Disease, Chpt. 15, pp. 335-347 (1988).

Crowe, Paul D. et al., "A Lymphotoxin-b-Specific Receptor," Science, vol. 264:707-708 (1994).

Crowe, Paul D. et al., "Production of lymphotoxin (LTa) and a soluble dimeric form of its receptor using the bacuipvirus expression system," Journal of Immunological Methods, vol. 168:79-89 (1994).

Damle, Nitin K. et al., "Distinct Regulatory Effects of IL-4 and TNF-a During CD3-Dependent and CD3-Independent Initiation of Human T-Cell Activation," Lymphokine Research, vol. 8(2):85-97 (1989).

Dhein, Jens et al., "Induction of Apoptosis by Monoclonal Antibody Anti-APO-1 Class Switch Variants is Dependent on Cross-linking of APO-1 Cell Surface Antigens," The Journal of Immunology, vol. 149(10):3166-3173 (1992).

Dighe, Anand S. et al., "Enhanced in Vivo Growth and Resistance to Rejection of Tumor Cells Expressing Dominant Negative IFNg Receptors," Immunity, vol. 1:447-456 (1994).

De Togni, Pietro et al., "Abnormal Development of Peripheral Lymphoid Organs in Mice Deficient in Lymphotoxin," Science, vol. 264:703-707 (1994).

Dijkstra, Christine D. et al., "Marginal zone macrophages identified by a monoclonal antibody: characterization of immuno- and enzyme-histochemical properties and functional capacities," Immunology, vol. 55:23-30 (1985).

Düzgünes, Nejat et al., "Liposome Targeting to HIV-Infected Cells Via Recombinant Soluble CD4 and CD4-IgG (Immunoadhesin)," Journal of Cellular Biochemistry, vol. 16:77, No. Q514 (1992).

Eck, Michael J. et al., "The Structure of Tumor Necrosis Factor-a at 2.6 Å Resolution, Implications for Receptor Binding," The Journal of Biological Chemistry, vol. 264(29):17595-17605 (1989).

Eck, Michael J. et al., "The Structure of Human Lymphotoxin (Tumor Necrosis Factor-b) at 1.9-Å Resolution," The Journal of Biological Chemistry, vol. 267(4):2119-2122 (1992).

Endres, Robert et al., "Mature Follicular Dendritic Cell Networks Depend on Expression of Lymphotoxin b Receptor by Radioresistant Stromal Cells and of Lymphotoxin b and Tumor Necrosis Factor by B Cells," J. Exp. Med., vol. 189 (1):159-167 (1999).

Eppstein, Deborah A. et al., "Biological activity of liposome-encapsulated murine interferon g is mediated by a cell membrane receptor," Proc. Natl. Acad. Sci. USA, vol. 82:3688-3692 (1985).

Erickson, Sharon L. et al., "Decreased sensitivity to tumour-necrosis factor but normal T-cell development in TNF receptor-2-deficient mice," Nature, vol. 372:560-563 (1994).

Ettinger, Rachel et al., "Disrupted splenic architecture, but normal lymph node development in mice expressing a soluble lymphotoxin-b receptor-IgG1 fusion protein," Proc. Natl. Acad. Sci. USA, vol. 93:13102-13107 (1996).

Fägerstam, Lars G. et al., "Surface Plasmon Resonance Detection in Affinity Technologies," Handbook of Affinity Chromatography, Chpt. 9, pp. 229-252 (1993).

Farrah, Terry et al., "Emerging cytokine family," Nature, vol. 358:26 (1992).

Fitch, F.W. et al., "Differential Regulation of Murine T Lymphocyte Subsets," Annu. Rev. Immunol., vol. 11:29-48 (1993).

Force, Walker R. et al., "Mouse Lymphotoxin-b Receptor," The Journal of Immunology, vol. 155:5280-5288 (1995).

Foy, Teresa M. et al., "gp39-CD40 Interactions Are Essential for Germinal Center Formation and the Development of B Cell Memory," J. Exp. Med., vol. 180:157-163 (1994).

Fu, Yang-Xin et al., "B Lymphocytes Induce the Formation of Follicular Dendritic Cell Clusters in a Lymphotoxin a-dependent Fashion," J. Exp. Med., vol. 187(7):1009-1018 (1998).

Fu, Yang-Xin et al., "Development and Maturation of Secondary Lymphoid Tissues," Annu. Rev. Immunol., vol. 17:399-433 (1999).

Fu, Yang-Xin et al., "Lymphotoxin-a (LTa) Supports Development of Splenic Follicular Structure That Is Required for IgG Responses," J. Exp. Med., vol. 185(12):2111-2120 (1997).

Fuh, Germaine et al., "Rational Design of Potent Antagonists to the Human Growth Hormone Receptor," Science, vol. 256:1677-1680 (1992).

Fukushima, Keiko et al., "N-Linked Sugar Chain Structure of Recombinant Human Lymphotoxin Produced by CHO Cells: The Functional Role of Carbohydrate as to Its Lectin-like Character and Clearance Velocity," Archives of Biochemistry and Biophysics, vol. 304(1):144-153 (1993).

Fütterer, Agnes et al., "The Lymphotoxin b Receptor Controls Organogenesis and Affinity Maturation in Peripheral Lymphoid Tissues," Immunity, vol. 9:59-70 (1998).

Gatanaga, Tetsuya et al., "Purification and characterization of an inhibitor (soluble tumor necrosis factor receptor) for tumor necrosis factor and lymphotoxin obtained from the serum ultrafiltrates of human cancer patients," Proc. Natl. Acad. Sci. USA, vol. 87:8781-8784 (1990).

Goeddel, D.V. et al., "Tumor Necrosis Factors: Gene Structure and Biological Activities," Cold Spring Harbor Symposia Quantitative Biology, vol. LI:597-609 (1986).

Gommerman, Jennifer L. et al., "Lymphotoxin/Light, Lymphoid Microenvironments and Autoimmune Disease," Nat. Rev. Immunol., vol. 3(8):642-655 (2003).

Gonzalez, Mercedes et al., "The Sequential Role of Lymphotoxin and B Cells in the Development of Splenic Follicles," J. Exp. Med., vol. 187(7):997-1007 (1998).

Goodwin, Raymond G. et al., "Molecular and Biological Characterization of a Ligand for CD27 Defines a New Family of Cytokines with Homology to Tumor Necrosis Factor," Cell, vol. 73:447-456 (1993).

Granger, Gale A. et al., "Lymphocyte in Vitro Cytotoxicity: Mechanisms of Immune and Non-Immune Small Lymphocyte Mediated Target L Cell Destruction," The Journal of Immunology, vol. 101(1):111-120 (1968).

Gray, Patrick W. et al., "Cloning and expression of cDNA for human lymphotoxin, a lymphokine with tumour necrosis activity," Nature, vol. 312:721-724 (1984).

Gray, Patrick W., "Molecular Characterization of Human Lymphotoxin," Lymphokines, vol. 13:199-208 (1987).

Green, Lora M. et al., "Cytotoxic Lymphokines Produced by Cloned Human Cytotoxic T Lymphocytes, I. Cytotoxins Produced by Antigen-Specific and Natural Killer-Like CTL Are Dissimilar to Classical Lymphotoxins," The Journal of Immunology, vol. 135(6):4034-4043 (1985).

Green, Lora M. et al., "Rapid Colorimetric Assay for Cell Viability: Application to the Quantitation of Cytotoxic and Growth Inhibitory Lymphokines," Journal of Immunological Methods, vol. 70:257-268 (1984).

Gupta, Manisha et al., "CD8-Mediated Protection against Evola Virus Infection Is Perforin Dependent," The Journal of Immunology, vol. 174:4198-4202 (2005).

Györfy, Z. et al., "Alteration of the TNF Sensitivity and Membrane Viscosity of Target Cells," Eur. Cytokine Netw., vol. 7(2):167 (1996).

Hagemeijer, A., "Cytogenics and oncogenes," Leukemia, vol. 6(Suppl. 4):16-18 (1992).

Han, Shuhua et al., "Cellular Interaction in Germinal Centers, Roles of CD40 Ligand and B7-2 in Established Germinal Centers," The Journal of Immunology, vol. 155:556-567 (1995).

Harris, William J. et al., "Therapeutic antibodies—the coming of age," TibTech, vol. 11:42-44 (1993).

Havell, Edward A. et al., "The Antitumor Function of Tumor Necrosis Factor (TNF) I. Therapeutic Action of TNF against an Established Murine Sarcoma Is Indirect, Immunologically Dependent, and Limited by Severe Toxicity," J. Exp. Med., vol. 167:1067-1085 (1988).

Heath, Sonya L. et al., "Follicular dendritic cells and human immunodeficiency virus infectivity," Nature, vol. 377:740-744 (1995).

Higuchi, Masahiro et al., "Inhibition of Ligand Binding and Antiproliferative Effects of Tumor Necrosis Factor and Lymphotoxin by Soluble Forms of Recombinant P60 and P80 Receptors," Biochemical and Biophysical Research Communications, vol. 182(2):638-643 (1992).

Hipp, Jason D. et al., "Cancer Vaccines: An Update," In Vivo, vol. 14:571-585 (2000).

Hiserodt, John C. et al., "Identification of Membrane-Associated Lymphotoxin (LT) on Mitogen-Activated Human Lymphocytes Using Heterologous Anti-LT Antisera in Vitro," Cellular Immunology, vol. 34:326-339 (1977).

Hober, Didier et al., "Serum Levels of Tumor Necrosis Factor-a (TNF-a), Interleukin-6 (IL-6), and Interleukin-1b (IL-1b) in Dengue-Infected Patients," Am. J. Trop. Med. Hyg., vol. 48(3):324-331 (1993).

Huang, Sui et al., "Immune Response in Mice That Lack the Interferon-g Receptor," Science, vol. 259:1742-1745 (1993).

Hwang, Karl J. et al., "Hepatic uptake and degradation of unilamellar sphingomyelin/cholesterol liposomes: A kinetic study," Proc. Natl. Acad. Sci. USA, vol. 77(7):4030-4034 (1980).

Itoh, Naoto et al., "The Polypeptide Encoded by the cDNA for Human Cell Surface Antigen Fas Can Mediate Apoptosis," Cell, vol. 66:233-243 (1991).

Jain, Rakesh K., "Vascular and interstitial barriers to delivery of therapeutic agents in tumors," Cancer and Metastasis Reviews, vol. 9:753-766 (1990).

Jalkanen, S. et al., "A Distinct Endothelial Cell Recognition System That Controls Lymphocyte Traffic into Inflamed Synovium," Science, vol. 233:556-558 (1986).

Johne, Bent et al., "Epitope mapping and binding kinetics of monoclonal antibodies studied by real time biospecific interaction analysis using surface plasmon resonance," Journal of Immunological Methods, vol. 160:191-198 (1993).

Jones, E.Y. et al., "Structure of tumour necrosis factor," Nature, vol. 338:225-228 (1989).

Juráková, Vera et al., "Interferon inducer, polyriboguanylic—polyribocytidylic acid, inhibits experimental hepatic metastases in mice," European Journal of Pharmacology, vol. 221:107-111 (1992).

Kasid, Attan et al., "Human gene transfer: Characterization of human tumor-infiltrating lymphocytes as vehicles for retroviral-mediated gene trasfer in man," Proc. Natl. Acad. Sci. USA, vol. 87:473-477 (1990).

Katz, Irene R. eta l., "Growth of SJL/J-Derived Transplantable Reticulum Cell Sarcoma as Related to Its Ability to Induce T-Cell Proliferation in the Host. III. Studies on Thymectomized and Congenitally Athymic SJL Mice," Cellular Immunology, vol. 65:84-92 (1981).

Katz, Jonathan D. et al., "T Helper Cell Subsets in Insulin-Dependent Diabetes," Science, vol. 268:1185-1188 (1995).

Kawabe, Tsutomu et al., "The Immune Responses in CD40-Deficient Mice: Impaired Immunoglobulin Class Switching and Germinal Center Formation," Immunity, vol. 1:167-178 (1994).

Kinkhabwala, M. et al., "A Novel Addition to the T Cell Repertory Cell Surface Expression of Tumor Necrosis Factor/Cachectin by Activated Normal Human T Cells," J. Exp. Med., vol. 171:941-946 (1990).

Kohno, Tadahiko et al., "A second tumor necrosis factor receptor gene product can shed a naturally occurring tumor necrosis factor inhibitor," Proc. Natl. Acad. Sci. USA, vol. 87:8331-8335 (1990).

Kolanus, Waldemar et al., "T Cell Activation by Clustered Tyrosine Kinases," Cell, vol. 74:171-183 (1993).

Kopp, William C. et al., "Immunomodulatory Effects of Interferon-g in Patients with Metastatic Malignant Melanoma," J. Immunother., vol. 13(3):181-190 (1993).

Kraal, Georg, "Cells in the Marginal Zone of the Spleen," International Review of Cytology, vol. 132:31-74 (1992).

Kraal, Georg et al., "Expression of the Mucosal Vascular Addressin, MAdCAM-1, on Sinus-Lining Cells in the Spleen," American Journal of Pathology, vol. 147(3):763-771 (1995).

Kraal, G. et al., "Lymphocyte migration in the spleen: the effect of macrophage elimination," Immunology, vol. 68:227-232 (1989).

Kraal, G. et al., "Marginal metallophilic cells of the mouse spleen identified by a monoclonal antibody," Immunology, vol. 58:665-669 (1986).

Kratz, Alexander et al., "Chronic Inflammation Caused by Lymphotoxin Is Lymphoid Neogenesis," J. Exp. Med., vol. 183:1461-1472 (1996).

Kriegler, M. et al., "A Novel Form of TNF/Cachectin Is a Cell Surface Cytotoxic Transmembrane Protein: Ramifications for the Complex Physiology of TNF," Cell, vol. 53:45-53 (1988).

Lacy, Mark D. et al., "Viral Hemorrhagic Fevers," Advances in Pediatric Infectious Diseases, vol. 12:21-53 (1997).

Laman, Jon D. et al., "Functions of CD40 and Its Ligand, gp39 (CD40L)," Critical Reviews in Immunology, vol. 16:59-108 (1996).

Lane, Peter et al., "Activated human T cells express a ligand for the human B cell-associated antigen CD40 which participates in T cell-dependent activation of B lymphocytes," Eur. J. Immunol., vol. 22:2573-2578 (1992).

Langer, Robert et al., "Biocompatibility of polymeric delivery systems for macromolecules," Journal of Biomedical Materials Research, vol. 15:267-277 (1981).

Langer, Robert, "Controlled release of macromolecules," Chemtech, pp. 98-105 (1982).

Lasky, J.L. et al., "Characterization and Growth Factor Requirements of SJL Lymphoma, I. Development of a B Cell Growth Factor-Dependent in Vitro Cell Line, cRCS-X," The Journal of Immunology, vol. 14:679-687 (1988).

Lasky, Jennifer L. et al., "Characterization and growth factor requirements of SJL lymphomas II. Interleukin 5 dependence on the in vitro cell line, cRCS-X, and influence of other cytokines," Eur. J. Immunol., vol. 19:365-371 (1989).

Lawton, Pornsri et al., "Characterization of the Mouse Lymphotoxin-b Gene," The Journal of Immunology, vol. 154:239-246 (1995).

Lazar, Eliane et al., "Transforming Growth Factor a: Mutation of Aspartic Acid 47 and Leucine 48 Results in Different Biological Activities," Molecular and Cellular Biology, vol. 8(3):1247-1252 (1988).

Le Hir, Michel et al., "Differentiation of Follicular Dendritic Cells and Full Antibody Responses Require Tumor Necrosis Factor Receptor-1 Signaling," J. Exp. Med., vol. 183:2367-2372 (1996).

Luettig, Birgit et al., "Evidence for the Existence of Two Forms of Membrane Tumor Necrosis Factor: An Integral Protein and a Molecule Attached to its Receptor," The Journal of Immunology, vol. 143(12):4034-4038 (1989).

Liang, Chi-Ming et al., "Production and Characterization of Monoclonal Antibodies Against Recombinant Human Tumor Necrosis Factor/Cachectin," Biochemical and Biophysical Research Communications, vol. 137(2):847-854 (1986).

Ling, Leona E. et al., "Human Type I Interferon Receptor, IFNAR, Is a Heavily Glycosylated 120-130 kD Membrane Protein," Journal of Interferon and Cytokine Research, vol. 15:55-61 (1995).

Liu, Chau-Ching et al., "Identification and characterization of a membrane-bound cytotoxin of murine cytolytic lymphocytes that is related to tumor necrosis factor/cachectin," Proc. Natl. Acad. Sci. USA, vol. 86:3286-3290 (1989).

Liu, Chau-Ching et al., "Identification, Isolation, and Characterization of a Novel Cytotoxin in Murine Cytolytic Lymphocytes," Cell, vol. 51:393-403 (1987).

Loetscher, Hansruedi et al., "Recombinant 55-kDa Tumor Necrosis Factor (TNF) Receptor," The Journal of Biological Chemistry, vol. 266(27):18324-18329 (1991).

MacKay, Fabienne et al., "Cytotoxic Activities of Recombinant Soluble Murine Lymphotoxin-a and Lymphotoxin-ab Complexes," The Journal of Immunology, vol. 159:3299-3310 (1997).

MacKay, Fabienne et al., "Lymphotoxin but not tumor necrosis factor functions to maintain splenic architecture and humoral responsiveness in adult mice," Eur. J. Immunol., vol. 27:2033-2042 (1997).

MacKay, Fabienne et al., "Turning off follicular dendritic cells," Nature, vol. 395:26-27 (1998).

MacLennan, I.C.M. et al., "The Structure and Function of Secondary Lymphoid Tissues," Clinical Aspects of Immunology, Blackwell Scientific Publications, 5th Edition, vol. 1, Chpt. 2, pp. 13-30 (1993).

Maeda, Kunihiko et al., "Murine Follicular Dendritic Cells and Low Affinity Fc Receptors for IgE (FceRII)," The Journal of Immunology, vol. 148(8):2340-2347 (1992).

Mallett, Susan et al., "A new superfamily of cell surface proteins related to the nerve growth factor receptor," Immunology Today, vol. 12(7):220-223 (1991).

Matsumoto, Mitsuru et al., "Affinity maturation without germinal centres in lymphotoxin-a-deficient mice," Nature, vol. 382:462-466 (1996).

Matsumoto, Mitsuru et al., "Distinct Roles of Lymphotoxin a and the Type 1 Tumor Necrosis Factor (TNF) Receptor in the Establishment of Follicular Dendritic Cells from the Non-Bone Marrow-derived Cells," J. Exp. Med., vol. 186 (12):1997-2004 (1997).

Matsumoto, Mitsuru et al., "Lymphotoxin-a-deficient and TNF receptor-I-deficient mice define developmental and functional characteristics of germinal centers," Immunological Reviews, vol. 156:137-144 (1997).

Matsumoto, Mitsuru et al., "Role of Lymphotoxin and the Type I TNF Receptor in the Formation of Germinal Centers," Science, vol. 271:1289-1291 (1996).

Mauri, Davide N. et al., "Light, a New Member of the TNF Superfamily, and Lymphotoxin a Are Ligands for Herpesvirus Entry Mediator," Immunity, vol. 8:21-30 (1998).

Mendlovic, Shlomo et al., "Induction of a systemic lupus erythematosus-like disease in mice by a common human anti-DNA idiotype," Proc. Natl. Acad. Sci. USA, vol. 85:2260-2264 (1988).

Miller, Glenn T. et al., "Specific Interaction of Lymphocyte Function-associated Antigen 3 with CD2 Can Inhibit T Cell Responses," J. Exp. Med., vol. 178:211-222 (1993).

Modlin, Robert L. et al., "Type 2 cytokines and negative immune regulation in human infections," Current Opinion in Immunology, vol. 5:511-517 (1993).

Mohan, Chandra et al., "Interaction Between CD40 and Its Ligand gp39 in the Development of Murine Lupus Nephritis," The Journal of Immunology, vol. 154:1470-1480 (1995).

Mohler, Kendall M. et al., "Suluble Tumor Necrosis Factor (TNF) Receptors Are Effective Therapeutic Agents in Lethal Endotoxemia and Function Simultaneously as Both TNF Carriers and TNF Antagonists," Journal of Immunology, vol. 151:1548-1561 (1993).

Montgomery, Rebecca I. et al., "Herpes Simplex Virus-1 Entry into Cells Mediated by a Novel Member of the TNF/NGF Receptor Family," Cell, vol. 87:427-436 (1996).

Morrison, Sherie L. et al., "Chimeric human antibody molecules: Mouse antigen-binding domains with human constant region domains," Proc. Natl. Acad. Sci. USA, vol. 81:6851-6855 (1984).

Morrison, Sherie L., "In Vitro Antibodies: Strategies for Production and Application," Annu. Rev. Immunol., vol. 10:239-265 (1992).

Morrissey, Philip J. et al., "CD4+ T Cells That Expess High Levels of CD45RB Induce Wasting Disease When Transferred into Congenic Severe Combined Immunodeficient Mice. Disease Development Is Prevented by Cotrasfer of Purified CD4+ T Cells," J. Exp. Med., vol. 178:237-244 (1993).

Nakache, Maurice et al., "The mucosal vascular addressin is a tissue-specific endothelial cell adhesion molecule for circulating lymphocytes," Nature, vol. 337:179-181 (1989).

Neumann, Brigitte et al., "Defective Peyer's Patch Organogenesis in Mice Lacking the 55-kD Receptor for Tumor Necrosis Factor," J. Exp. Med., vol. 184:259-264 (1996).

Ngo, J. Thomas et al., "Computational Complexity, Protein Structure Prediction, and the Levinthal Paradox," The Protein Folding Problem and Tertiary Structure Prediction, Birkhauer, Kenneth M. Merz, Jr. (Ed.), Chpt. 14, pp. 433-506 (1994).

Nicola, Anthony V. et al., "Monoclonal Antibodies to Distinct Sites on Herpes Simplex Virus (HSV) Glycoprotein D Block HSV Binding to HVEM," Journal of Virology, vol. 72(5):3595-3601 (1998).

Niederle, Norbert et al., "Long-Term Treatment of Chronic Myelogenous Leukemia with Different Interferons: Results from Three Studies," Leukemia and Lymphoma, vol. 9:111-119 (1993).

Old, Lloyd J., "Tumor Necrosis Factor (TNF)," Science, vol. 230:630-632 (1985).

Onishi, Tetsuro et al., "A Study on Direct Antitumor Activity of Bropirimine (Oral Interferon Inducer) for Renal Cell Carcinoma," Acta Urol. Jpn., vol. 40:195-200 (1994).

Pasparakis, Manolis et al., "Immune and Inflammatory Responses to TNFa Deficient Mice: A Critical Requirement for TNFa in Germinal Centre Formation and in the Maturation of the Humoral Immune Response," Eur. Cytokine Network, vol. 7(2):239, No. 132 (1996).

Pass, Harvey I. et al., "The Macrophage, TNF, and Other Cytokines," Basic Biology for the Thoracic Surgeon, vol. 5 (1):73-90 (1995).

Paul, Nina L. et al., "Lymphotoxin Activation by Human T-Cell Leukemia Virus Type I-Infected Cell Lines: Role of NF-kB," Journal of Virology, vol. 64(11):5412-5419 (1990).

Paul, Nina L. et al., "Lymphotoxin," Ann. Rev. Immunol., vol. 6:407-438 (1988).

Pennica, Diane et al., "Human tumour necrosis factor: precursor structure, expression and homology to lymphotoxin," Nature, vol. 312:724-729 (1984).

Peppel, Karsten et al., "A Tumor Necrosis Factor (TNF) Receptor-IgG Heavy Chain Chimeric Protein as a Bivalent Antagonist of TNF Activity," J. Exp. Med., vol. 171:1483-1489 (1991).

Peterson, Andrew et al., "Monoclonal antibody and ligand binding sites of the T cell erythrocyte receptor (CD2)," Nature, vol. 329:842-846 (1987).

Pfeffer, Klaus et al., "Mice Deficient for the 55 kd Tumor Necrosis Factor Receptor Are Resistant to Endotoxic Shock, yet Succumb to *L. monocytogenes* Infection," Cell, vol. 73:457-467 (1993).

Picarella, Dominic E. et al., "Insulitis in transgenic mice expressing tumor necrosis factor b (lymphotoxin) in the pancreas," Proc. Natl. Acad. Sci. USA, vol. 89:10036-10040 (1992).

Picker, Louis J. et al., "Physiological and Molecular Mechanisms of Lymphocyte Homing," Annu. Rev. Immunol., vol. 10:561-591 (1992).

Pleskov, V.M. et al., "The receptor-mediated endocytosis of influenza viruses and low-density lipoproteins by tissue cells," Vopr. Virusol., vol. 39(3):121-125 (1994).

Pociot, F. et al., "A Tumour Necrosis Factor Beta Gene Polymorphism in Relation to Monokine Secretion and Insulin-Dependent Diabetes Mellitus," Scand. J. Immunol., vol. 33:37-49 (1991).

Ponzio, Nicholas M. et al., "Host-Tumor Interactions in the SJL Lymphoma Model," Intern. Rev. Immunol., vol. 1:273-301 (1986).

Powell, Kenneth L. et al., "The antiviral effects of nitric oxide," Trends in Microbiology, vol. 3(3):81-88 (1995).

Powrie, Fiona et al., "Inhibition of Th1 Responses Prevents Inflammatory Bowel Disease in scid Mice Reconstituted with CD45RBhi CD4+ T Cells," Immunity, vol. 1:553-562 (1994).

Powrie, Fiona et al., "Phenotypically distinct subsets of CD4+ T cells induce or protect from chronic intestinal inflammation in C. B-17 scid mice," International Immunology, vol. 5(11):1461-1471 (1993).

Qin, Zhihai et al., "Human Lymphotoxin Has at Least Equal Antitumor Activity in Comparison to Human Tumor Necrosis Factor but Is Less Toxic in Mice," Blood, vol. 85(10):2779-2785 (1995).

Queen, Cary et al., "A humanized antibody that binds to the interleukin 2 receptor," Proc. Natl. Acad. Sci. USA, vol. 86:10029-10033 (1989).

Raitano, Arthur B. et al., "Tumor Necrosis Factor Up-regulates g-Interferon Binding in a Human Carcinoma Cell Line," The Journal of Biological Chemistry, vol. 265(16):10466-10472 (1990).

Ranges, Gerald E. et al., "Tumor Necrosis Factor-a AS a Proliferative Signal for an IL-2-Dependent T Cell Line: Strict Species Specificity of Action," The Journal of Immunology, vol. 142:1203-1208 (1989).

Ranges, Gerald E. et al., "Tumor Necrosis Factor a/Cachectin is a Growth Factor for Thymocytes, Synergistic Interactions with Other Cytokines," J. Exp. Med., vol. 167:1472-1478 (1988).

Reed, Steven G. et al., "T-cell and cytokine responses in leishmaniasis," Current Opinion in Immunology, vol. 5:524-531 (1993).

Reisfeld, Ralph A. et al., "Involvement of B Lymphocytes in the Growth Inhibition of Human Pulmonary Melanoma Metastases in Athymic nu/nu Mice by an Antibody-Lymphotoxin Fusion Protein," Cancer Research, vol. 56:1707-1712 (1996).

Rennert, P.D. et al., "Normal Development of Lymph Nodes is Disrupted by Soluble LT beta Receptor—Ig Fusion Protein," European Cytokine Network, vol. 7(2):167, No. 17 (1996).

Rennert, Paul D. et al., "Surface Lymphotoxin a/b Complex Is Required for the Development of Peripheral Lymphoid Organs," J. Exp. Med., vol. 184:1999-2006 (1996).

Renshaw, Blair R. et al., "Humoral Immune Response in CD40 Ligand-deficient Mice," J. Exp. Med., vol. 180:1889-1900 (1994).

Reutershealth, "Systemic Lupus Erythematosus," retrieved online at http://www.reutershealth.com/wellconnected/doc63.html (2002).

Roitt, Ivan M. et al., "Antibody Effector Functions," Immunology, Third Edition, Mosby, p. 4.8 (1993).

Roitt, Ivan M. et al., "Introduction to the Immune System," Immunotogy, Third Edition, Mosby, Chpt. 1, pp. 1.1-1.12 (1993).

Roitt, Ivan M. et al., "Hypersensitivity—Type I," Immunology, Third Edition, Mosby, Chpt. 19, pp. 19.1-19.22 (1993).
Romagnani, Sergio, "Lymphokine Production by Human T Cells in Disease States," Annu. Rev. Immunol., vol. 12:227-257 (1994).
Roodman, G. David et al., "Tumor Necrosis Factor-alpha and Hematopoietic Progenitors: Effects of Tumor Necrosis Factor on the Growth of Erythroid Progenitors CFU-E and BFU-E and the Hematopoietic Cell Lines K562, HL60, and HEL Cells," Exp. Hematol., vol. 15:928-935 (1987).
Rosenberg, Steven A. et al., "Use of Tumor-infiltrating Lymphocytes and Interleukin-2 in the Immunotherapy of Patients with Metastatic Melanoma," The New England Journal of Medicine, vol. 319(25):1676-1680 (1988).
Rothe, Joachim et al., "Mice lacking the tumour necrosis factor receptor 1 are resistant to TNF-mediated toxicity but highly susceptible to infection by *Listeria monocytogenes*," Nature, vol. 364:798-802 (1993).
Ruddle, Nancy H. et al., "An Antibody to Lymphotoxin and Tumor Necrosis Factor Prevents Transfer of Experimetnal Allergic Encephalomyelitis," J. Exp. Med., vol. 172:1193-1200 (1990).
Ruddle, Nancy H. et al., "Cytotoxicity Mediated by Soluble Antigen and Lymphocytes in Delayed Hypersensitivity, III. Analysis of Mechanism," The Journal of Experimental Medicine, vol. 128:1267-1279 (1968).
Ruddle, Nancy H., "Lymphotoxin redux," Immunology Today, vol. 6(5):156-159 (1985).
Ruddle, Nancy H. et al., "The Role of Lymphotoxin in Inflammation," Prog. Allergy, vol. 40:162-182 (1988).
Rudikoff, Stuart et al., "Single amino acid substitution altering antigen-binding specificity," Proc. Natl. Acad. Sci. USA, vol. 79:1979-1983 (1982).
Sanchez, Anthony et al., "Analysis of Human Peripheral Blood Samples from Fatal and Nonfatal Cases of Ebola (Sudan) Hemorrhagic Fever: Cellular Responses, Virus Load, and Nitric Oxide Levels," Journal of Virology, vol. 78 (19):10370-10377 (2004).
Sastry, K. Jagannadha et al., "HIV-1 tat Gene Induces Tumor Necrosis Factor-b (Lymphotoxin) in a Human B-lymphoblastoid Cell Line," The Journal of Biological Chemistry, vol. 265(33):20091-20093 (1990).
Sayegh, Mohamed H. et al., "CD28-B7 Blockade after Alloantigenic Challenge in Vivo Inhibits Th1 Cytokines but Spares Th2," J. Exp. Med., vol. 181:1869-1874 (1995).
Schall, Thomas J. et al., "Molecular Cloning and Expression of a Receptor for Human Tumor Necrosis Factor," Cell, vol. 61:361-370 (1990).
Scheurich, Peter et al., "Immunoregulatory Activity of Recombinant Human Tumor Necrosis Factor (TNF)-a: Induction of TNF Receptors on Human T Cells and TNF-a-Mediated Enhancement of T Cell Responses," The Journal of Immunology, vol. 138(6):1786-1790 (1987).
Schiller, Joan H. et al., "Biological and Clinical Effects of Intravenous Tumor Necrosis Factor-a Administered Three Times Weekly," Cancer Research, vol. 51:1651-1658 (1991).
Schoenfeld, Hans-Joachim et al., "Efficient Purification of Recombinant Human Tumor Necrosis Factor b from *Escherichia coli* Yields Biologically Active Protein with a Trimeric Structure That Binds to Both Tumor Necrosis Factor Receptors," The Journal of Biological Chemistry, vol. 266(6):3863-3869 (1991).
Schriever, Folke et al., "The Central Role of Follicular Dendritic Cells in Lymphoid Tissues," Advances in Immunology, vol. 51:243-284 (1992).
Séité, Paule et al., "BCL2 Gene Activation and Protein Expression in Follicular Lymphoma: a Report on 64 Cases," Leukemia, vol. 7(3):410-417 (1993).
Selmaj, Krzysztof et al., "Identification of Lymphotoxin and Tumor Necrosis Factor in Multiple Sclerosis Lesions," J. Clin. Invest., vol. 87:949-954 (1991).
Shalaby, M. Rafaat et al., "The Involvement of Human Tumor Necrosis Factors-a and -b in the Mixed Lymphocyte Reaction," The Journal of Immunology, vol. 141(2):499-503 (1988).
Sheehan, Kathleen C.F. et al., "Generation and Characterization of Hamster Monoclonal Antibodies that Neutralize Murine Tumor Necrosis Factors," The Journal of Immunology, vol. 142(11):3884-3893 (1989).
Shehadeh, Naim N. et al., "Altered Cytokine Activity in Adjuvant Inhibition of Autoimmune Diabetes," Journal of Autoimmunity, vol. 6:291-300 (1993).
Sidman, Kenneth R. et al., "Controlled Release of Macromolecules and Pharmaceuticals from Synthetic Polypeptides Based on Glutamic Acid," Biopolymers, vol. 22:547-556 (1983).
Sigel, Morton B. et al., "Production of Antibodies by Inoculation into Lymph Nodes," Methods in Enzymology, vol. 93:3-12 (1983).
Slepushkin, A.N. et al., "A comparative study of live and inactivated influenza vaccines: the organization of the observation and the results of a study of their reactogenicity and immunogenicity," Vopr. Virusol., vol. 39(3):128-131 (1994).
Smith, Craig A. et al., "A Receptor for Tumor Necrosis Factor Defines an Unusual Family of Cellular and Viral Proteins," Science, vol. 248:1019-1023 (1990).
Smith, Craig A. et al., "The TNF Receptor Superfamily of Cellular and Viral Proteins: Activation, Costimulation, and Death," Cell, vol. 76(6):959-962 (1994).
Spriggs, David R. et al., "Tumor Necrosis Factor Expression in Human Epithelial Tumor Cell Lines," J. Clin. Invest., vol. 81:455-460 (1988).
Tartaglia, Louis a. et al., "Two TNF receptors," Immunology Today, vol. 13(5):151-153 (1992).
Tavernier, Jan et al., "Conserved residues of tumour necrosis factor and lymphotoxin constitute the framework of the trimeric structure," FEBS, vol. 257(2):315-318 (1989).
Tew, John G. et al., "Follicular Dendritic Cells as Accessory Cells," Immunological Reviews, vol. 117:185-211 (1990).
Thomas, H. et al., "Biological Approaches to Cancer Therapy," The Journal of International Medical Research, vol. 17:191-204 (1989).
Tibbetts, Randal S. et al., "Cardiac Antigen-Specific Autoantibody Production is Associated with Cardiomyopathy in *Trypanosoma cruzi*-infected mice," Journal of Immunology, vol. 152:1493-1499 (1994).
Toellner, Kai-Michael et al., "Immunoglobulin Swith Transcript Production In Vivo Related to the Site and Time of Antigen-specific B Cell Activation," J. Exp. Med., vol. 183:2303-2312 (1996).
Traunecker, André et al., "Highly efficient neutralization of HIV with recombinant CD4-immunoglobulin molecules," Nature, vol. 339:68-70 (1989).
Trethewey, Pat, "Systemic Lupus Erythematosus," Dimensions of Critical Care Nursing, vol. 23(3):111-115 (2004).
Tschachler, Erwin et al., "Constitutive Expression of Lymphotoxin (Tumor Necrosis Factor b) in HTLV-I-Infected Cell Lines," Human Retrovirology HTLV, Raven Press, Ltd., William A. Blattner (Ed.), pp. 105-113 (1990).
Tsiagbe, V.K. et al., "Syngeneic Response to SJL Follicular Center B Cell Lymphoma (Reticular Cell Sarcoma) Cells Is Primarily in Vb16+ CD4+ T Cells," The Journal of Immunology, vol. 150:5519-5528 (1993).
Tsiagbe, V.K. et al., "The Physiology of Germinal Centers," Critical Reviews in Immunology, vol. 16:381-421 (1996).
Turner, Martin et al., "Human T cells from autoimmune and normal individuals can produce tumor necrosis factor," Eur. J. Immunol., vol. 17:1807-1814 (1987).
Ullrich, Axel et al., "Signal Transduction by Receptors with Tyrosine Kinase Activity," Cell, vol. 61:203-212 (1990).
Van Dullemen, Hendrik M. et al., "Treatment of Crohn's Disease With Anti-Tumor Necrosis Factor Chimeric Monoclonal Antibody (cA2)," Gastroenterology, vol. 109:129-135 (1995).
Van Kooten, Cees et al., "CD40-CD40 Ligand: A Multifunctional Receptor—Ligand Pair," Advances in Immunology, vol. 61:1-77 (1996).
Van Vliet, Els et al., "Reticular Fibroblasts in Peripheral Lymphoid Organs Identified by a Monoclonal Antibody," The Journal of Histochemistry and Cytochemistry, vol. 34(7):883-890 (1986).
Ware, Carl F. et al., "Expression of Surface Lymphotoxin and Tumor Necrosis Factor on Activated T, B, and Natural Killer Cells," The Journal of Immunology, vol. 149(12):3881-3888 (1992).

Ware, Carl F. et al., "Human T Cell Hybridomas Producing Cytotoxic Lymphokines: Induction of Lymphotoxin Release and Killer Cell Activity by Anti-CD3 Monoclonal Antibody or Lectins and Phorbol Ester," Lymphokine Research, vol. 5 (4):313-324 (1986).

Ware, Carl F. et al., "Mechanisms of Lymphocyte-mediated Cytotoxicity II. Biochemical and Serologic Identification of a Precursor Lymphotoxin Form (pre-LT) Produced by MLC-Sensitized Human T Lymphocytes In Vitro," The Journal of Immunology, vol. 126(5):1927-1933 (1981).

Ware, Carl F. et al., "Regulation of the CTL Lytic Pathway by Tumor Necrosis Factor," Cellular Immunity and the Immunotherapy of Cancer, pp. 121-128 (1990).

Ware, C.F. et al., "The Ligands and Receptors of the Lymphotoxin System," Curr. Top. Microbiol. Immunol., vol. 198:175-218 (1995).

Warfield, Kelly L. et al., "Induction of Humoral and CD8+ T Cell Responses Are Required for Protection against Lethal Ebola Virus Infection," The Journal of Immunology, vol. 175:1184-1191 (2005).

Warzocha, Krzysztof et al., "Mechanisms of action of the tumor necrosis factor and lymphotoxin ligand-receptor system," Eur. Cytokine Netw., vol. 5(6):83-96 (1994).

Watanabe-Fukunaga, Rie et al., "Lymphoproliferation disorder in mice explained by defects in Fas antigen that mediates apoptosis," Nature, vol. 356:314-317 (1992).

Winter, Greg et al., "Man-made antibodies," Nature, vol. 349:293-299 (1991).

Wong, G.H.W. et al., "Strategies for Manipulating Apoptosis for Cancer Therapy With Tumor Necrosis Factor and Lymphotoxin," Journal of Cellular Biochemistry, vol. 60:56-60 (1996).

Wong, Grace H.W. et al., "Tumour necrosis factor a and b inhibit virus replication and synergize with interferons," Nature, vol. 323:819-822 (1986).

Wu, Qiang et al., "The Requirement of Membrane Lymphotoxin for the Presence of Dendritic Cells in Lymphoid Tissues," J. Exp. Med., vol. 190(5):629-638 (1999).

Wysocki, L.J. et al., "'Panning' for lymphocytes: A method for cell selection," Proc. Natl. Acad. Sci. USA, vol. 75 (6):2844-2848 (1978).

Xu, Jianchao et al., "Mice Deficient for teh CD40 Ligand," Immunity, vol. 1:423-431 (1994).

Yonehara, Shin et al., "A Cell-killing monoclonal antibody (Anti-Fas) to a Cell Surface Antigen Co-downregulated with the Receptor of Tumor Necrosis Factor," J. Exp. Med., vol. 169:1747-1756 (1989).

Zhou, M. et al., "Real-Time Measurements of Kinetics of EGF Binding to Soluble EGF Receptor Monomers and Dimers Support the Dimerization Model for Receptor Activation," Biochemistry, vol. 32:8193-8198 (1993).

Ziff, Morris, "Emigration of Lymphocytes in Rheumatoid Synovitis," Advances in Inflammation Research, vol. 12:1-9 (1988).

European Search Report for Application No. 04017208.2, 4 pages, dated Jun. 19, 2012.

* cited by examiner

| | | | | | |
|---|---|---|---|---|---|
| 1 | SQPQAVPPYA | SENQTCRDQE | KEYYEPQHRI | CCSRCPPGTY | VSAKCSRIRD | 50 |
| 51 | TVCATCAENS | YNEHWNYLTI | CQLCRPCDPV | MGLEEIAPCT | SKRKTQCRCQ | 100 |
| 101 | PGMFCAAWAL | ECTHCELLSD | CPPGTEAELK | DEVGKGNNHC | VPCKAGHFQN | 150 |
| 151 | TSSPSARCQP | HTRCENQGLV | EAAPGTAQSD | TTCKNPLEPL | PPEMSGT | 197 |

US 8,455,445 B2

METHODS FOR INHIBITING LYMPHOTOXIN-β RECEPTOR SIGNALING IN TH1 CELL-ASSOCIATED DISORDERS

This application is a continuation of U.S. application Ser. No. 11/982,415, which was filed on Oct. 31, 2007, now issued as U.S. Pat. No. 7,951,371 on May 31, 2011, which is a continuation of Ser. No. 10/077,406, which was filed on Feb. 15, 2002, now issued as U.S. Pat. No. 7,427,403, which is a divisional of U.S. application Ser. No. 09/000,166, filed on Jun. 8, 1998, now issued as U.S. Pat. No. 6,403,087, which is a 35 U.S.C. §371 filing of International Application Number PCT/US96/12010 which was filed on Jul. 19, 1996, which claims priority to U.S. application Ser. No. 08/505,606, filed on Jul. 21, 1995, now issued as U.S. Pat. No. 5,925,351. The contents of the aforementioned applications are hereby incorporated herein by reference.

TECHNICAL FIELD OF THE INVENTION

This invention relates to compositions and methods comprising "lymphotoxin-β receptor blocking agents", which block lymphotoxin-β receptor signalling. Lymphotoxin-β receptor blocking agents are useful for treating lymphocyte-mediated immunological diseases, and more particularly, for inhibiting Th1 cell-mediated immune responses. This invention relates to soluble forms of the lymphotoxin-β receptor extracellular domain that act as lymphotoxin-β receptor blocking agents. This invention also relates to the use of antibodies directed against either the lymphotoxin-β receptor or its ligand, surface lymphotoxin, that act as lymphotoxin-β receptor blocking agents. A novel screening method for selecting soluble receptors, antibodies and other agents that block LT-β receptor signalling is provided.

BACKGROUND OF THE INVENTION

The pattern of cytokines released at the onset of an immune challenge can affect the subsequent choice of which immune effector pathways are activated. The choice between immune effector mechanisms is mediated by CD4-positive helper T lymphocytes (T helper cells or Th cells). Th cells interact with antigen-presenting cells (APCs), which display peptide fragments of processed foreign antigen in association with MHC class II molecules on their surfaces. Th cells are activated when they recognize particular epitopes of a foreign antigen displayed on the appropriate APC surface for which the Th cells express a specific receptor. Activated Th cells, in turn, secrete cytokines (lymphokines) which activate appropriate immune effector mechanisms.

Th cells can activate diverse effector mechanisms, including killer T cell activation B cell antibody production and macrophage activation. The choice between effector mechanisms is mediated largely by which cytokines are produced by the activated Th cells.

Th cells can be divided into three subgroups based on their cytokine secretion patterns (Fitch et al., *Ann. Rev. Immunol.*, 11, pp. 29-48 (1993)). These subgroups are called Th0, Th1 and Th2. In the mouse, non-stimulated "naive" T helper cells produce IL-2. Short term stimulation leads to Th0 precursor cells, which produce a wide range of cytokines including IFN-γ, IL-2, IL-4, IL-5 and IL-10. Chronically-stimulated Th0 cells can differentiate into either Th1 or Th2 cell types, whereupon the cytokine expression pattern changes.

Some cytokines are released by both Th1 and Th2 cells (e.g., IL-3, GM-CSF and TNF). Other cytokines are made exclusively by one or the other Th cell subgroup. The specialized effects of T helper cell subgroups were first recognized in mouse. A similar subdivision of T helper cells also exists in humans (Romagnani et al., *Ann. Rev. Immunol.*, 12, pp. 227-57 (1994)).

Th1 cells produce LT-α, IL-2 and IFN-γ. In humans, the Th1 pattern of cytokine secretion has been generally associated with cellular immunity and resistance to infection. The Th1 cytokines tend to activate macrophages and certain inflammatory responses such as Type IV "delayed type" hypersensitivity (see below). Th1 cytokines play an important role in cellular rejection of tissue grafts and organ transplants.

Th2 cells produce the cytokines IL-4, IL-5, IL-6 and IL-10. Th2 cytokines increase eosinophil and mast cell production and promote the full expansion and maturation of B cells (Howard et al., "T cell-derived cytokines and their receptors", *Fundamental Immunology*, 3d ed., Raven Press, New York (1993)). Th2 cytokines also enhance antibody production, including IgE antibodies associated with allergic responses and anti-graft antibodies. Th2 cells may also participate in immune suppression and tolerance to persistent antigens.

Th1- and Th2-associated cytokines play a role in certain hypersensitivity responses—inappropriate or disproportionate immune responses evoked upon contact with a previously encountered antigen. There are four recognized types of hypersensitivity (Roitt et al., Immunology, pp. 19.1-22.12 (Mosby-Year Book Europe Ltd., 3d ed. 1993)).

Type I "immediate hypersensitivity" involves allergen-induced Th2 cell activation and Th2 cytokine release. The Th2 cytokine IL-4 stimulates B cells to undergo isotype switching to produce IgE, which activates mast cells to produce acute Inflammatory reactions such as those which lead to eczema, asthma and rhinitis.

Types II and III hypersensitivity are caused by IgG and IgM antibodies directed against cell surface or specific tissue antigens (Type II) or soluble serum antigens (Type III). These types of hypersensitivity reactions are not thought to be mediated by Th cells.

Type IV "delayed type" hypersensitivity (DTH) is Th1 cell mediated. DTH reactions take more than 12 hours to develop and are referred to as "cell-mediated" because they can be transferred between mice by transferring Th1 cells but not serum alone. Type IV DTH responses are generally classified into three types: contact, tuberculin-type and granulomatous hypersensitivity.

Many cell-mediated responses that can cause disease are inducible in healthy mice by transferring lymphocytes from a diseased mouse (e.g., insulin-dependent diabetes and experimental autoimmune encephalitis). This feature distinguishes Type IV DTH from the other three types of hypersensitivity, which are humoral immune responses caused primarily by antibodies which can be transferred in cell-free serum.

T helper cells also participate in the regulation of de novo immunoglobulin isotype switching. Different Th subsets may influence the relative proportion of immunoglobulins of a given isotype produced in response to immune challenge. For example, the Th2 cytokine IL-4 can switch activated B cells to the IgG1 isotype and suppress other isotypes. As discussed above, IL-4 also activates IgE overproduction in type I hypersensitivity reactions. The Th2 cytokine IL-5 induces the IgA isotype. These Th2 cytokine effects on isotype switching are counter-balanced by IFN-γ produced by Th1 cells.

The differential patterns of cytokines secreted by Th1 and Th2 cells appear to direct a response towards different immune effector mechanisms. The switch that activates either a cell-mediated or humoral effector mechanism is sensitized by cross-suppression between Th1 and Th2 cells: IFN-γ produced by Th1 cells inhibits Th2 cell proliferation and Th2 cell-secreted IL-10 appears to reduce cytokine secretion from Th1 cells.

Depending on the relative affinities of the cytokines for their molecular targets, the Th1 and Th2 negative regulatory circuits may amplify the effects of small concentration differences between Th1 and Th2 cytokines. An amplified Th1 or Th2 cytokine signal may trigger the switch between cell-mediated or humoral effector mechanisms based on small changes in the relative concentrations of Th1 and Th2 cytokines. The ability to control this switch by modulating the relative concentrations of Th1 and Th2 cytokines would be useful for treating imbalances in a variety of Th1 and Th2 cell-dependent immune responses which can lead to immune disorders and diseases.

Pathological Th1 responses are associated with a number of organ-specific and systemic autoimmune conditions, chronic inflammatory diseases, and delayed type hypersensitivity reactions. As discussed above, Th1 responses also contribute to cellular responses leading to grafted tissue and transplanted organ rejection.

The treatment of these various Th1 cell-based immunological conditions to date has generally employed immunomodulatory and immuno suppressive agents as well as a number of drugs with poorly characterized mechanisms (e.g., gold or penicillamine). Three general immunosuppressive agents used currently are steroids, cyclosporine and azathioprine.

Steroids are pleiotropic anti-inflammatory agents which suppress activated macrophages and inhibit the activity of antigen presenting cells in ways which reverse many of the effects of the Th1 cytokine IFN-$\gamma$. Cyclosporine—a potent immunosuppressive agent—suppresses cytokine production and reduces the expression of IL-2 receptors on lymphocytes during their activation. Azathioprine is an anti-proliferative agent which inhibits DNA synthesis. These non-specific immunosuppressive agents are generally required in high doses which increase their toxicity (e.g. nephro- and hepatotoxicity) and cause adverse side effects. They are thus unsuitable for long term therapies.

To address the problems caused by conventional treatments with non-specific immunosuppressive agents, many current therapeutic strategies aim at suppressing or activating selective aspects of the immune system. An especially attractive goal is the manipulation of the balance between Th1 and Th2 cytokines to shift the balance between cell-mediated and humoral effector mechanisms.

To accomplish a shift between cell-mediated and humoral effector mechanisms, it would be useful to be able to modulate the activity of a molecule that can shift the relative activities of Th1 and Th2 cell subclasses. Candidates for such molecules include the cytokines and their receptors. Recent data suggest that LT-$\alpha$, IL-12, IFN-$\alpha$ and IFN-$\gamma$ favor the development of Th1 responses, whereas IL-1 and IL-4 polarize a response towards a Th2 effector mechanism (Romagnani at al., *Ann. Rev. Immunol.*, 12, pp. 227-57 (1994)).

Many of the Th cell cytokines are pleiotropic regulators of immune development and function, and inhibiting their production would have deleterious effects on non-T cell mediated responses. A desirable and effective target for selectively modulating the choice between Th1 and Th2 effector mechanisms has not been identified.

SUMMARY OF THE INVENTION

The present invention solves the problems referred to above by providing pharmaceutical compositions and methods for treating immunological diseases by inhibiting lymphotoxin-$\beta$ receptor (LT-$\beta$-R) signalling using lymphotoxin-$\beta$ receptor blocking agents. More particularly, the compositions and methods comprising LT-$\beta$-R blocking agents are useful for inhibiting Th1 cell-mediated immune responses such as, for example, inflammatory bowel syndrome.

In one embodiment, soluble forms of the lymphotoxin-$\beta$ receptor extracellular domain that act as LT-$\beta$-R blocking agents are provided. The preferred compositions and methods of this embodiment comprise a recombinant lymphotoxin-B receptor fusion protein that has the LT-$\beta$-R extracellular ligand binding domain fused to an immunoglobulin constant heavy chain domain. More preferably, the LT-$\beta$-R ligand binding domain is fused to a human IgG Fc domain.

In another embodiment of this invention, antibodies that act as LT-$\beta$-R blocking agents are provided. Preferred compositions and methods of this embodiment comprise one or more antibodies directed against the lymphotoxin-$\beta$ receptor. More preferably, the antibody is a monoclonal antibody. Other preferred compositions and methods of this embodiment comprise one or more antibodies directed against surface lymphotoxin. More preferably, the antibody is a monoclonal antibody directed against lymphotoxin-$\beta$.

This invention further provides a novel screening process for selecting LT-$\beta$-R blocking agents—such as soluble forms of the LT-$\beta$-R, anti-LT Abs and anti-LT-$\beta$-R Abs. This screening process involves performing tumor cell cytotoxicity assays that monitor LT-$\beta$-R signalling. The assay makes use of the increased sensitivity of human adenocarcinoma cells to ligand- or antibody-induced LT-$\beta$-R signalling in the presence of an LT-$\beta$-R activating agent (such as LT-$\alpha$1/$\beta$2) in a tumor cytotoxicity assay.

LT-$\beta$-R blocking agents inhibit the cytotoxic effects of LT-$\alpha$/$\beta$ heteromeric complexes (or other LT-$\beta$-R activating agents) on tumor cells. The procedure used to test putative LT-$\beta$-R blocking agents is exemplified for the case of anti-LT-$\beta$-R antibodies (in the presence of the LT-$\beta$-R activating agents LT-$\alpha$1/$\beta$2) and comprises the following steps:

1) Tumor cells (e.g., HT29 human adenocarcinoma cells) are cultured for several days in media containing IFN-$\gamma$ and purified LT-$\alpha$1/$\beta$2 in the presence or absence of the particular anti-LT-$\beta$-R Ab being assayed;

2) The cells are treated with a dye that stains living cells; and

3) The number of stained cells is quantitated to determine the fraction of tumor cells killed in the presence of LT-$\alpha$1/$\beta$2, IFN-$\gamma$ and the test anti-LT-$\beta$-R Ab in each sample. Alternatively, the number of surviving cells can be determined by any of a number of well-known assays which measure cell viability, such as $^3$H-thymidine incorporation into DNA. An anti-LT-$\beta$-R Ab (or an Ab combination) that decreases the percentage of tumor cells killed in this assay by at least 20% is a LT-$\beta$-R blocking agent within the scope of this invention.

This cytolytic assay may be performed using LT-$\alpha$/$\beta$ heteromeric complexes and other LT-$\beta$-R activating agents, either alone or in combination. The assay can also be adapted as required to identify new LT-$\beta$-R blocking agents.

DETAILED DESCRIPTION OF THE INVENTION

Figures 1, 2:
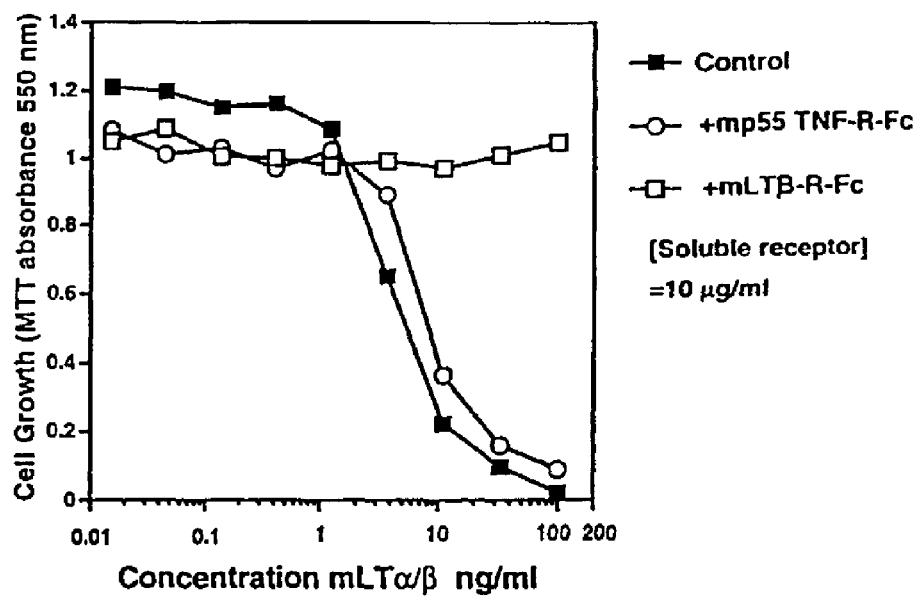
FIG. 1. The sequence of the extracellular portion of the human LT-$\beta$ receptor which encodes the ligand binding domain (SEQ ID NO:1).
FIG. 2. A soluble murine LT-$\beta$ receptor coupled to the human IgG1 Fc domain (mLT-$\beta$-R-Fc) blocks LT-$\beta$-R signalling in mouse WEHI 164 cells induced by soluble murine LT-$\alpha$/$\beta$ ligand. WEHI 164 cells are killed as a function of increasing LT ligand (mLT-α/β) concentration. Soluble mLT-β-R-Fc (10 µg/ml) blocks this LT ligand-induced cell death. A soluble murine TNF receptor fusion protein (p55TNF-R-Fc) has little effect on blocking LT-α/β-activated cell death. Growth was quantitated after three days by measuring the optical density (OD 550) of reacted MTT, which is proportional to cell number.

In order that the invention herein described may be fully understood, the following detailed description is set forth.

The term "cytokine" refers to a molecule which mediates interactions between cells. A "lymphokine" is a cytokine released by lymphocytes.

The term "T helper (Th) cells" refers to a functional subclass of T cells which help to generate cytotoxiC T Cells and which cooperate with B cells to stimulate antibody production. Helper T cells recognize antigen in association with class II MHC molecules.

The term "Th1" refers to a subclass of T helper cells that produce LT-α, interferon-γ and IL-2 (and other cytokines) and which elicit inflammatory reactions associated with a cellular, i.e. non-immunoglobulin, response to a challenge.

The term "Th2" refers to a subclass of T helper cells that produce cytokines, including IL-4, IL-5, IL-6 and IL-10, which are associated with an immunoglobulin (humoral) response to an immune challenge.

The term "cell mediated" refers to those immunological events that result from the direct effects of T cells and their products to produce a response. This type of response is generally (but not exclusively) associated with the Th1 class of T cells. Not included in this category would be the helper effects of T cells on B cell differentiation and B cell expansion, which are generally associated with the Th2 class of T cells.

The term "delayed type hypersensitivity (DTH)" refers to an immunological response that is characterized by a slow response to an antigen with the full effect manifesting itself over a 1-3 day period. This slow response is in contrast to the relatively fast response seen in an immunoglobulin-mediated (humoral) allergic reaction. There are three types of DTH reactions: contact hypersensitivity, tuberculin-type hypersensitivity and granulomatous reactions.

The terms "Immunoglobulin response" or "humoral response" refer to the immunological response of an animal to a foreign antigen whereby the animal produces antibodies to the foreign antigen. The Th2 class of T helper cells are critical to the efficient production of high affinity antibodies.

The term "Fc domain" of an antibody refers to a part of the molecule comprising the hinge, CH2 and CH3 domains, but lacking the antigen binding sites. The term is also meant to include the equivalent regions of an IgM or other antibody isotype.

The term "anti-LT-B receptor antibody" refers to any antibody that specifically binds to at least one epitope of the LT-β receptor.

The term "anti-LT antibody" refers to any antibody that specifically binds to at least one epitope of LT-α, LT-β or a LT-α/β complex.

The term "LT-β-R signalling" refers to molecular reactions associated with the LT-β-R pathway and subsequent molecular reactions which result therefrom.

The term "LT-β-R blocking agent" refers to an agent that can diminish ligand binding to LT-β-R, cell surface LT-β-R clustering or LT-β-R signalling, or that can influence how the LT-β-R signal is interpreted within the cell.

A LT-β-R blocking agent that acts at the step of ligand-receptor binding can inhibit LT ligand binding to the LT-β-R by at least 20%. A LT-β-R blocking agent that acts after the step of ligand-receptor binding can inhibit the cytotoxic effects of LT-β-R activation on a tumor cell by at least 20%. Examples of LT-β-R blocking agents include soluble LT-β-R-Fc molecules, and anti-LT-α, anti-LT-β, anti-LT-α/β and anti-LT-β-R Abs. Preferably, the antibodies do not cross-react with the secreted form of LT-α.

The term "LT-β-R biological activity" refers to: 1) the ability of the LT-β-R molecule or derivative to compete for soluble or surface LT ligand binding with soluble or surface LT-β-R molecules; or
2) the ability to stimulate an immune regulatory response or cytotoxic activity in common with a native LT-β-R molecule.

The terms "LT-α/β heteromeric complex" and "LT heteromeric complex" refer to a stable association between at least one LT-α and one or more LT-β subunits, including soluble, mutant, altered and chimeric forms of one or more of the subunits. The subunits can associate through electrostatic, van der WaalS, or covalent interactions. Preferably, the LT-α/β heteromeric complex has at least two adjacent LT-β subunits and lacks adjacent LT-α subunits. When the LT-α/β heteromeric complex serves as a LT-β-R activating agent in a cell growth assay, the complex is preferably soluble and has the stoichiometry LT-α1/β2. Soluble LT-α/β heteromeric complexes lack a transmembrane domain and can be secreted by an appropriate host cell which has been engineered to express LT-α and/or LT-β subunits (Crowe et al., *J. Immunol. Methods*, 168, pp. 79-89 (1994)).

The term "LT ligand" refers to a LT heteromeric complex or derivative thereof that can specifically bind to the LT-β receptor.

The term "LT-β-R ligand binding domain" refers to the portion or portions of the LT-β-R that are involved in specific recognition of and interaction with a LT ligand.

The terms "surface LT-α/β complex" and "surface LT complex" refer to a complex comprising LT-α and membrane-bound LT-β subunits—including mutant, altered and chimeric forms of one or more of the subunits—which is displayed on the cell surface. "Surface LT ligand" refers to a surface LT complex or derivative thereof that can specifically bind to the LT-β receptor.

The term "subject" refers to an animal, or to one or more cells derived from an animal. Preferably, the animal is a mammal. Cells may be in any form, including but not limited to cells retained in tissue, cell clusters, immortalized, transfected or transformed cells, and cells derived from an animal that have been physically or phenotypically altered.

Lymphotoxin-β: A Member of the TNF Family

Tumor Necrosis Factor (TNF)-related cytokines have emerged as a large family of pleiotropic mediators of host defense and immune regulation. Members of this family exist in membrane-bound forms which act locally through cell-cell contact, or as secreted proteins which can act on distant targets. A parallel family of TNF-related receptors react with these cytokines and trigger a variety of pathways including cell death, cell proliferation, tissue differentiation and proinflammatory responses.

TNF, lymphotoxin-α (LT-α, also called TNF-β) and lymphotoxin-β (LT-β) are members of the TNF family of ligands, which also includes the ligands to the Fas, CD27, CD30, CD40, OX-40 and 4-1BB receptors (Smith et al., *Cell*, 76, pp. 959-62 (1994)). Signalling by several members of the TNF family—including TNF, LT-α, LT-β and Fas—can induce tumor cell death by necrosis or apoptosis (programmed cell death). In non-tumorigenic cells, TNF and many of the TNF family ligand-receptor interactions influence immune system development and responses to various immune challenges.

Most TNF family ligands are found as a membrane-bound form on the cell surface. TNF and LT-α are found in both secreted and membrane-associated surface forms in humans. Surface TNF has a transmembrane region that is proteolytically cleaved to generate the secreted form. In contrast, surface LT-α lacks a transmembrane region. Membrane-associated LT-α is tethered to the cell surface as a heteromeric complex with LT-β, a related transmembrane polypeptide, in a LT-α/β complex.

Most membrane-associated LT-α/β complexes ("surface LT") have a LT-α1/β2 stoichiometry (Browning et al., *Cell*, 72, pp. 847-56 (1993); Browning et al., *J. Immunol.*, 154, pp. 33-46 (1995)). Surface LT ligands do not bind TNF-R with high affinity and do not activate TNF-R signalling. Another TNF-related receptor, called the LT-β receptor (LT-β-R), binds these surface lymphotoxin complexes with high affinity (Crowe et al., *Science*, 264, pp. 707-10 (1994)).

LT-β-R signalling, like TNF-R signalling, has anti-proliferative effects and can be cytotoxic to tumor cells. In applicants' co-pending U.S. application Ser. No. 08/378,968, compositions and methods for selectively stimulating LT-β-R using LT-β-R activating agents are disclosed. LT-β-R activating agents are useful for inhibiting tumor cell growth without co-activating TNF-R-induced proinflammatory or immunoregulatory pathways.

In non-tumor cells, TNF and TNF-related cytokines are active in a wide variety of immune responses. Both TNF and LT-α ligands bind to and activate TNF receptors (p55 or p60 and p75 or p80; herein called "TNF-R"). TNF and LT-α are produced by macrophages in an early and rapid response to microbial infection which enhances the microbicidal activity of macrophages and neutrophils. TNF and LT-α made by macrophages or cytotoxic T lymphocytes (CTLs or "killer T cells") bind to TNF receptors on target cell surfaces and trigger the death of susceptible cells.

TNF and TNF-related cytokines can also initiate inflammatory cascades in response to infection or stress. The release of TNF, LT-α and IFN-γ changes the adhesion properties between the vascular endothelial cells and certain lymphocyte types. Increased adhesion facilitates phagocyte and leucocyte migration from the bloodstream into the tissues surrounding an inflammation site. Similar inflammatory reactions play a major role in cellular rejection of tissue grafts and organ transplants, and in certain immune disorders.

Cell surface lymphotoxin (LT) complexes have been characterized in $CD4^+$ T cell hybridoma cells (II-23.D7) which express high levels of LT (Browning et al., *J. Immunol.*, 147, pp. 1230-37 (1991); Androlewicz et al., *J. Biol. Chem.*, 267, pp. 2542-47 (1992)). The expression and biological roles of LT-β-R, LT subunits and surface LT complexes have been reviewed in C. F. Ware et al., "The ligands and receptors of the lymphotoxin system", in *Pathways for Cytolysis. Current Topics Microbiol. Immunol.*, Springer-Verlag, pp. 175-218 (1995).

LT-α expression is induced and LT-α secreted primarily by activated T and B lymphocytes and natural killer (NK) cells. Among the T helper cell subclasses, LT-α appears to be produced by Th1 but not Th2 cells. LT-α has also been detected in melanocytes. Microglia and T cells in lesions of multiple sclerosis patients can also be stained with anti-LT-α antisera.

Lymphotoxin-β (also called p33), has been identified on the surface of T lymphocytes, T cell lines, B cell lines and lymphokine-activated killer (LAK) cells. LT-β is the subject of applicants' co-pending international applications PCT/US91/04588, published Jan. 9, 1992 as WO 92/00329; and PCT/US93/11669, published Jun. 23, 1994 as WO 94/13808, which are herein incorporated by reference.

Surface LT complexes are primarily expressed by activated T and B lymphocytes and natural killer (NK) cells as defined by FACS analysis or immunohistology using anti-LT-α antibodies or soluble LT-β-R-Fc fusion proteins. Surface LT has also been described on human cytotoxic T lymphocyte (CTL) clones, activated peripheral mononuclear lymphocytes (PML), IL-2-activated peripheral blood lymphocytes (LAK cells), pokeweed mitogen-activated or anti-CD40-activated peripheral B lymphocytes (PBL) and various lymphoid tumors of T and B cell lineage. Engagement of alloantigen-bearing target cells specifically induces surface LT expression by $CD8^+$ and $CD4^+$ CTL clones.

The LT-β receptor, a member of the TNF family of receptors, specifically binds to surface LT ligands. LT-β-R binds LT heteromeric complexes (predominantly LT-α1/β2 and LT-α2/β1) but does not bind TNF or LT-α (Crowe et al., *Science*, 264, pp. 707-10 (1994)). Signalling by LT-β-R may play a role in peripheral lymphoid organ development and in humoral immune responses.

Studies on LT-β-R expression are in their early stages. LT-β-R mRNAs are found in human spleen, thymus and other major organs LT-β-R expression patterns are similar to those reported for p55-TNF-R except that LT-β-R is lacking on peripheral blood T cells and T cell lines.

Production of Soluble LT Complexes

Soluble LT-α/â heteromeric complexes comprise LT-â subunits which have been changed from a membrane-bound to a soluble form. These complexes are described in detail in applicants' co-pending international application (PCT/US93/11669, published Jun. 23, 1994 as WO 94/13808). Soluble LT-â peptides are defined by the amino acid sequence of lymphotoxin-â wherein the sequence is cleaved at any point between the end of the transmembrane region (i.e. at about amino acid #44) and the first TMF homology region (i.e. at amino acid #88) according to the numbering system of Browning et al., Cell, 72, pp. 847-56 (1993).

Soluble LT-â polypeptides may be produced by truncating the N-terminus of LT-â to remove the cytoplasmic tail and transmembrane region (Crowe et al., Science, 264, pp. 707-710 (1994)). Alternatively, the transmembrane domain may be inactivated by deletion, or by substitution of the normally hydrophobic amino acid residues which comprise a transmembrane domain with hydrophilic ones. In either case, a substantially hydrophilic hydropathy profile is created which will reduce lipid affinity and improve aqueous solubility. Deletion of the transmembrane domain is preferred over substitution with hydrophilic amino acid residues because it avoids introducing potentially immunogenic epitopes.

The deleted or inactivated transmembrane domain may be replaced with or attached to a type I leader sequence (e.g. the VCAM-1 leader) such that the protein is secreted beginning with a sequence anywhere from between val40 to pro88. Soluble LT-â polypeptides may include any number of well-known leader sequences at the N-terminus. Such a sequence would allow the peptides to be expressed and targeted to the secretion pathway in a eukaryotic system. See, e.g., Ernst et al., U.S. Pat. No. 5,082,783 (1992).

Soluble LT-α/â heteromeric complexes may be produced by co-transfecting a suitable host cell with DNA encoding LT-α and soluble LT-â (Crowe et al., J. Immunol. Methods, 168, pp. 79-89 (1994)). Soluble LT-â secreted in the absence of LT-α is highly oligomerized. However, when co-expressed with LT-α, a 70 kDa trimeric-like structure is formed which contains both proteins. It is also possible to produce soluble LT-α1/â2 heteromeric complexes by transfecting a cell line which normally expresses only LT-α (such as the RPMI 1788 cells discussed above) with a gene encoding a soluble LT-â polypeptide.

LT-α and LT-â polypeptides may be separately synthesized, denatured using mild detergents, mixed together and renatured by removing the detergent to form mixed LT heteromeric complexes which can be separated (see below).

Purification of LT-α1/â2 Complexes

Soluble LT-α1/â2 heteromeric complexes are separated from co-expression complexes comprising a different subunit stoichiometry by chromatography using TNF and LT-â receptors as affinity purification reagents. The TNF receptors only bind within α/α clefts of LT complexes. The LT-â receptor binds with high affinity to â/â clefts, and with lower affinity to α/â clefts of heteromeric LT-α/â complexes. Accordingly, LT-α3 and LT-α2/â1 will bind to TNF-R. The LT-â-R can also bind LT-α2/â1 trimers (within the α/â clefts) but cannot bind LT-α3. In addition, the LT-â-R (but not TNF-R) binds LT-α1/â2 and LT-ân (the exact composition of such preparation is unknown, however, they are large aggregates).

The receptor affinity reagents can be prepared as either a soluble extracellular domain (see for example Loetscher et al., J. Biol. Chem., 266, pp. 18324-29 (1991)), or as chimeric proteins with the extracellular ligand binding domain coupled to an immunoglobulin Fc domain (Loetscher et al., J. Biol. Chem., 266, pp. 18324-29 (1991); Crowe et al., Science, 264; pp. 707-710 (1994)). Receptors are coupled to affinity matrices by chemical cross-linking using routine procedures.

There are two schemes by which the LT-α1/â2 ligand can be purified using receptors and immuno-affinity chromatography. In the first scheme, a supernatant from an appropriate expression system co-expressing both LT-α and the truncated LT-â form is passed over a TNF-R column. The TNF-R will bind LT-α3 and LT-α2/â1 trimers. The flow through from the TNF-R column will contain LT-â(n) and LT-α1/â2.

In the second scheme, all LT-A-containing forms (LT-â(n). LT-α1/â2 and LT-α2/â1) are bound to and eluted from a LT-â-R column using classical methods such as chaotrophe or pH change. (LT-α3 flows through this column). The eluate is neutralized or the chaotrophe removed, and the eluate is then passed over a TNF-R column, which binds only to the LT-α2/â1 trimers. The flow through of this column will contain LT-â(n) and LT-α1/â2 trimers.

In both cases, pure LT-α1/â2 trimers can be separated from LT-â by subsequent gel filtration and/or ion exchange chromatographic procedures known to the art.

Alternatively, different forms of LT-α/â heteromeric complexes can be separated and purified by a variety of conventional chromatographic means. It may also be preferable to combine a series of conventional purification schemes with one of the immunoaffinity purification steps described above.

Screening For LT-β-R Blocking Agents

In one embodiment of this invention, the LT-β-R blocking agent comprises an antibody (Ab) directed against LT-β-R that inhibits LT-β-R signalling. Preferably, the anti-LT-β-R Ab is a monoclonal antibody (mAb). One such inhibitory anti-LT-β-R mAb is BDA8 mAb.

Inhibitory anti-LT-β-R Abs and other LT-β-R blocking agents can be identified using screening methods that detect the ability of one or more agents either to bind to the LT-β-R or LT ligand, or to inhibit the effects of LT-β-R signalling on cells.

One screening method makes use of the cytotoxic effects of LT-β-R signalling on tumor cells bearing the LT-β-R. Tumor cells are exposed to one or more LT-β-R activating agents to induce LT-β-R signalling. LT-β-R activating agents include LT-α/β heteromeric complexes (preferably soluble LT-α1/β2) in the presence of IFN-γ, or an activating anti-LT-β-R Ab (see below; also described in applicants' co-pending U.S. application Ser. No. 08/378,968). Antibodies and other agents that can block LT-β-R signalling are selected based on their ability to inhibit the cytotoxic effect of LT-β-R signalling on tumor cells in the following assay:

1) Tumor cells such as HT29 cells are cultured for three to four days in a series of tissue culture wells containing media and at least one LT-β-R activating agent in the presence or absence of serial dilutions of the agent being tested;

2) A vital dye stain which measures mitochondrial function such as NTT is added to the tumor cell mixture and reacted for several hours;

3) The optical density of the mixture in each well is quantitated at 550 nm wavelength light (OD 550). The OD 550 is proportional to the number of tumor cells remaining in the presence of the LT-β-R activating agent and the test LT-β-R blocking agent in each well. An agent or combination of agents that can reduce LT-β-R-activated tumor cell cytotoxicity by at least 20% in this assay, is a LT-β-R blocking agent within the scope of this invention.

Any agent or combination of agents that activate LT-β-R signalling can be used in the above assay to identify LT-β-R blocking agents. LT-β-R activating agents that induce LT-β-R signalling (such as activating anti-LT-β-R mAbs) can be selected based on their ability—alone or in combination with other agents—to potentiate tumor cell cytotoxicity using the tumor cell assay described above.

Another method for selecting an LT-β-R blocking agent is to monitor the ability of the putative agent to directly interfere with LT ligand-receptor binding. An agent or combination of agents that can block ligand-receptor binding by at least 20% is an LT-β-R blocking agent within the scope of this invention.

Any of a number of assays that measure the strength of ligand-receptor binding can be used to perform competition assays with putative LT-β-R blocking agents. The strength of the binding between a receptor and ligand can be measured using an enzyme-linked immunoadsorption assay (ELISA) or a radio-immunoassay (RIA). Specific binding may also be measured by fluorescently labelling antibody-antigen complexes and performing fluorescence-activated cell sorting (FACS) analysis, or by performing other such immunodetection methods, all of which are techniques well known in the art.

The ligand-receptor binding interaction may also be measured with the BIAcore instrument (Pharmacia Biosensor) which exploits plasmon resonance detection (Zhou at al., *Biochemistry*, 32, pp. 8193-98 (1993); Faegerstram and O'Shannessy, "Surface plasmon resonance detection in affinity technologies", in *Handbook of Affinity Chromatography*, pp. 229-52, Marcel Dekker, Inc., New York (1993)).

The BIAcore technology allows one to bind receptor to a gold surface and to flow ligand over it. Plasmon resonance detection gives direct quantitation of the amount of mass bound to the surface in real time. This technique yields both on and off rate constants and thus a ligand-receptor dissociation constant and affinity constant can be directly determined in the presence and absence of the putative LT-β-R blocking agent.

With any of these or other techniques for measuring receptor-ligand interactions, one can evaluate the ability of a LT-β-R blocking agent, alone or in combination with other agents, to inhibit binding of surface or soluble LT ligands to surface or soluble LT-β-R molecules. Such assays may also be used to test LT-β-R blocking agents or derivatives of such agents (e.g. fusions, chimeras, mutants, and chemically altered forms)—alone or in combination—to optimize the ability of that altered agent to block LT-β-R activation.

Production of Soluble LT-β-R Molecules

The LT-β-R blocking agents in one embodiment of this invention comprise soluble LT-β receptor molecules. FIG. 1 shows the sequence of the extracellular portion of the human LT-β-R, which encodes the ligand binding domain. Using the sequence information in FIG. 1 and recombinant DNA techniques well known in the art, functional fragments encoding the LT-β-R ligand binding domain can be cloned into a vector and expressed in an appropriate host to produce a soluble LT-β-R molecule. Soluble LT-β-R molecules that can compete with native LT-β receptors for LT ligand binding according to the assays described herein are selected as LT-β-R blocking agents.

A soluble LT-β receptor comprising amino acid sequences selected from those shown in FIG. 1 may be attached to one or more heterologous protein domains ("fusion domain") to increase the in vivo stability of the receptor fusion protein, or to modulate its biological activity or localization.

Preferably; stable plasma proteins—which typically have a half-life greater than 20 hours in the circulation—are used to construct the receptor fusion proteins. Such plasma proteins include but are not limited to: immunoglobulins, serum albumin, lipoproteins, apolipoproteins and transferrin. Sequences that can target the soluble LT-β-R molecule to a particular cell or tissue type may also be attached to the LT-β-R ligand binding domain to create a specifically-localized soluble LT-β-R fusion protein.

All or a functional portion of the LT-β-R extracellular region (FIG. 1) comprising the LT-β-R ligand binding domain may be fused to an immunoglobulin constant region like the Fc domain of a human IgG1 heavy chain (Browning et al., *J. Immunol.*, 154, pp. 33-46 (1995)). Soluble receptor-IgG fusion proteins are preferable, and are common immunological reagents, and methods for their construction are known in the art (see e.g., U.S. Pat. No. 5,225,538 incorporated herein by reference).

A functional LT-β-R ligand binding domain may be fused to an immunoglobulin (Ig) Fc domain derived from an immunoglobulin class or subclass other than IgG1. The Fc domains of antibodies belonging to different Ig classes or subclasses can activate diverse secondary effector functions. Activation occurs when the Fc domain is bound by a cognate Fc receptor. Secondary effector functions include the ability to activate the complement system, to cross the placenta, and to bind various microbial proteins. The properties of the different classes and subclasses of immunoglobulins are described in Roitt et al., *Immunology*, p. 4.8 (Mosby-Year Book Europe Ltd., 3d ed. 1993).

Activation of the complement system initiates cascades of enzymatic reactions that mediate inflammation. The products of the complement system have a variety of functions, including binding of bacteria, endocytosis, phagocytosis, cytotoxicity, free radical production and solubilization of immune complexes.

The complement enzyme cascade can be activated by the Fc domains of antigen-bound IgG1, IgG3 and IgM antibodies. The Fc domain of IgG2 appears to be less effective, and the Fc domains of IgG4, IgA, IgD and IgE are ineffective at activating complement. Thus one can select a Fc domain based on whether its associated secondary effector functions are desirable for the particular immune response or disease being treated with the LT-β-R-Fc fusion protein.

If it would be advantageous to harm or kill the LT ligand-bearing target cell, one could select an especially active Fc domain (IgG1) to make the LT-β-R-Fc fusion protein. Alternatively, if it would be desirable to target the LT-β-R-Fc fusion to a cell without triggering the complement system, an inactive IgG4 Fc domain could be selected.

Mutations in Fc domains that reduce or eliminate binding to Fc receptors and complement activation have been described (S. Morrison, *Annu. Rev. Immunol.*, 10, pp. 239-65 (1992)). These or other mutations can be used, alone or in combination, to optimize the activity of the Fc domain used to construct the LT-β-R-Fc fusion protein.

The production of a soluble human LT-β-R fusion protein comprising ligand binding sequences fused to a human immunoglobulin Fc domain (hLT-β-R-Ft) is described in Example 1. One CHO line made according to Example 1 that secretes hLT-β-R-Fc is called "hLTβ; R-hG1 CHO#14". A sample of this line was deposited on Jul. 21, 1995 with the American Type Culture Collection (ATCC) (Rockville, Md.) according to the provisions of the Budapest Treaty and was assigned the ATCC accession number CRL11965.

The production of a soluble murine LT-β-R fusion molecule (mLT-β-R-Fc) is described in Example 2. A CHO line made according to Example 2 that secretes mLT-β-R-Fc is called "mLTβ; R-hG1 CHO#1.3.BB". A sample of this line was deposited on Jul. 21, 1995 with the American Type Culture Collection (ATCC) (Rockville, Md.) according to the provisions of the Budapest Treaty and was assigned the ATCC accession number CRL11964.

All restrictions on the availability to the public of the above ATCC deposits will be irrevocably removed upon the granting of a patent on this application.

Different amino acid residues forming the junction point of the receptor-Ig fusion protein may alter the structure, stability and ultimate biological activity of the soluble LT-S receptor fusion protein. One or more amino acids may be added to the C-terminus of the selected LT-β-R fragment to modify the junction point with the selected fusion domain.

The N-terminus of the LT-β-R fusion protein may also be varied by changing the position at which the selected LT-β-R DNA fragment is cleaved at its 5' end for insertion into the recombinant expression vector. The stability and activity of each LT-β-R fusion protein may be tested and optimized using routine experimentation and the assays for selecting LT-β-R blocking agents described herein.

Using the LT-β-R ligand binding domain sequences within the extracellular domain shown in FIG. 1, amino acid sequence variants may also be constructed to modify the affinity of the soluble LT-β receptor or fusion protein for LT ligand. The soluble LT-β-R molecules of this invention can compete for surface LT ligand binding with endogenous cell surface LT-β receptors. It is envisioned that any soluble molecule comprising a LT-β-R ligand binding domain that can compete with cell surface LT-β receptors for LT ligand binding is a LT-β-R blocking agent that falls within the scope of the present invention.

Soluble LT-β-R Molecules as LT-β-R Blocking Agents

A soluble human LT-β receptor-immunoglobulin fusion protein (hLT-β-R-Fc) was made according to the procedures in Example 1 and tested for its ability to block LT-β-R-induced cytotoxicity in human HT29 tumor cells. Table 1 (Example 3) compares the ability of soluble LT-β receptor (hLT-β-R-Fc) and TNF receptor (p55-TNF-R-Fc) fusion proteins to block the inhibitory effects of various TNF and soluble LT ligands on HT29 tumor cell growth.

The data in Table 1 indicate the concentrations at which a soluble LT-β receptor. (hLT-β-R-Fc) can block the tumor cell death caused by interaction between LT-α1/β2 ligand and cell surface LT-β receptors by 50%. The ability to block tumor cell growth at least 20% identifies this soluble LT-β receptor as a LT-β-R blocking agent according to this invention. As expected, the soluble TNF-R fusion protein (p55-TNF-R-Fc) completely blocked TNF-induced growth inhibition by binding to TNF and preventing its interaction with surface receptor.

The soluble TNF-R fusion protein had no effect on LT ligand (LT-α1/β2)-mediated anti-proliferative effects. In contrast, the LT-β-R fusion protein blocked LT ligand effects but not the effects of TNF or LT-α. Thus soluble human LT-β-R fusion proteins do not interfere with TNF-R activation by TNF and LT-α ligands To determine whether LT-β-R signalling is also cytotoxic to tumor cells in mice, and whether soluble LT-β-R fusion proteins can block LT-β-R-induced cytotoxicity, a similar experiment was performed using mouse tumor cells. A soluble murine LT-β-R-Fc fusion protein (mLT-β-R-Fc; see Example 2) was tested for its ability to block the death of mouse WEHI 164 cells treated with LT ligand (Example 4).

FIG. 2 shows the effects of the soluble murine LT-β-R (mLT-β-R-Fc) on LT ligand-induced LT-β-R signalling in mouse WEHI 164 cells. As this assay indicates, WEHI 164 cells are killed by treatment with soluble LT-α1/β2 ligand. Addition of mLT-β-R-Fc blocks LT ligand-activated cell death. The control. TNF receptor fusion protein (p55TNF-R-Fc) has little effect on blocking cell death.

These data show that a soluble LT-β-R fusion protein can effectively compete with surface LT-β-R molecules for LT ligand binding. The soluble mLT-β-R-Fc fusion protein thus acts as a LT-β-R blocking agent in mice.

Source of Anti-Human LT-β-R Antibodies

In another embodiment of this invention, antibodies directed against the human LT-β receptor (anti-LT-β-R Abs) function as LT-β-R blocking agents. The anti-LT-β-R Abs of this invention can be polyclonal or monoclonal (mAbs) and can be modified to optimize their ability to block LT-β-R signalling, their in vivo bioavailability, stability, or other desired traits.

Polyclonal antibody sera directed against the human LT-β receptor are prepared using conventional techniques by injecting animals such as goats, rabbits, rats, hamsters or mice subcutaneously with a human LT-β receptor-Fc fusion protein (Example 1) in complete Freund's adjuvant, followed by booster intraperitoneal or subcutaneous injection in incomplete Freund's. Polyclonal antisera containing the desired antibodies directed against the LT-β receptor are screened by conventional immunological procedures.

Mouse monoclonal antibodies (mAbs) directed against a human LT-Z receptor-Fc fusion protein are prepared as described in Example 5. A hybridoma cell line (BD-A8.AB9) which produces the mouse anti-human LT-β-R mAb BDA8 was deposited on Jan. 12, 1995 with the American Type Culture Collection (ATCC) (Rockville, Md.) according to the provisions of the Budapest Treaty, and was assigned the ATCC accession number HB11798. All restrictions on the availability to the public of the above ATCC deposits will be irrevocably removed upon the granting of a patent on this application.

Various forms of anti-LT-β-R antibodies can also be made using standard recombinant DNA techniques (Winter and Milstein, Nature, 349, pp. 293-99 (1991)). For example, "chimeric" antibodies can be constructed in which the antigen binding domain from an animal antibody is linked to a human constant domain (e.g. Cabilly et al., U.S. Pat. No. 4,816,567; Morrison et al., Proc. Natl. Acad. Sci. U.S.A., 81, pp. 6851-55 (1984)). Chimeric antibodies reduce the observed immunogenic responses elicited by animal antibodies when used in human clinical treatments.

In addition, recombinant "humanized antibodies" which recognize the LT-β-R can be synthesized. Humanized antibodies are chimeras comprising mostly human IgG sequences into which the regions responsible for specific antigen-binding have been inserted (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter-species) sequences in human antibodies, and are less likely to elicit immune responses in the treated subject.

Construction of different classes of recombinant anti-LT-β-R antibodies can also be accomplished by making chimeric or humanized antibodies comprising the anti-LT-β-R variable domains and human constant domains (CH1, CH2, CH3)

isolated from different classes of immunoglobulins. For example, anti-LT-β-R IgM antibodies with increased antigen binding site valencies can be recombinantly produced by cloning the antigen binding site into vectors carrying the human μ chain constant regions (Arulanandam et al., *J. Exp. Med.*, 177, pp. 1439-50 (1993); Lane et al., *Eur. J. Immunol.*, 22, pp. 2573-78 (1993); Traunecker et al., *Nature*, 339, pp. 68-70 (1989)).

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modelling (Queen et al., *Proc. Natl. Acad. Sci.* 86, pp. 10029-33 (1989); WO 94/04679).

It may be desirable to increase or to decrease the affinity of anti-LT-β-R Abs for the LT-β-R depending on the targeted tissue type or the particular treatment schedule envisioned. For example, it may be advantageous to treat a patient with constant levels of anti-LT-β-R Abs with reduced ability to signal through the LT-β pathway for semi-prophylactic treatments. Likewise, inhibitory anti-LT-β-R Abs with increased affinity for the LT-β-R may be advantageous for short-term treatments.

Anti-LT-β-R Antibodies as LT-β-R Blocking Agents

Anti-LT-β-R antibodies that act as LT-β-R blocking agents may be selected by testing their ability to inhibit LT-β-R-induced cytotoxicity in tumor cells (Example 5).

Figure 3:
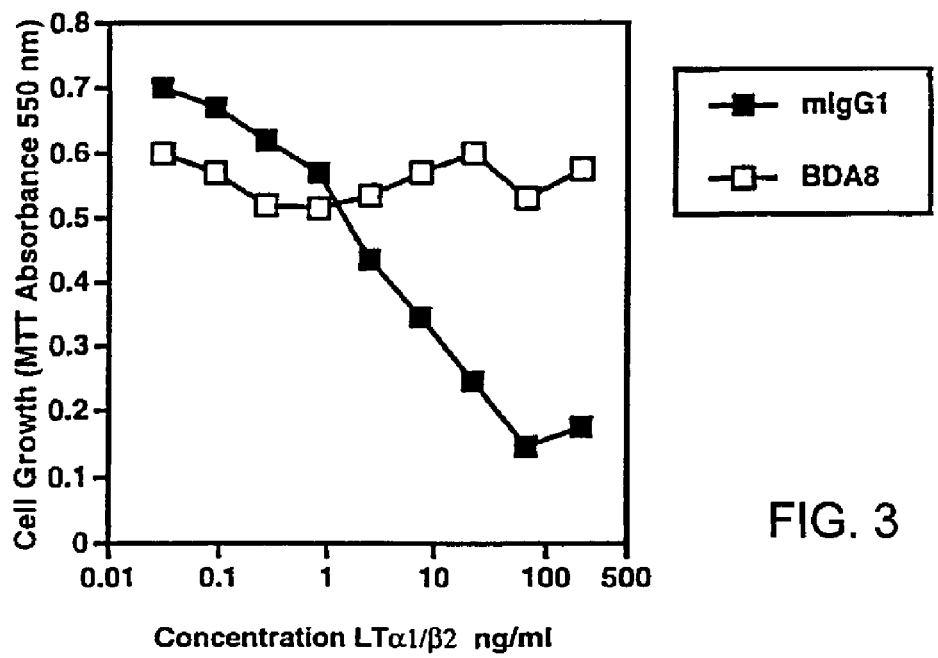
FIG. 3. An antibody directed against human LT-β-R (BDA8 mAb) blocks the interaction between soluble LT ligand and LT-β-R on a human cell surface. The growth of WiDr tumor cells is blocked by a combination of IFN-γ and soluble LT-α1/β2 ligand. The anti-LT-β-R antibody BDA8 blocks the ability of LT-α1/β2 ligand to inhibit the growth of WiDr tumor cells. Solid symbols show cell growth in the presence of IgG1 control mAb (10 µg/ml). Open symbols show the effects of anti-LT-β-R mAb BDA8 (10 µg/ml).

In a preferred embodiment of this invention, compositions and methods comprise the mouse anti-human LT-β-R mAb BDA8. FIG. 3 shows that mAb BDA8 acts as a LT-β-R blocking agent as defined by this invention. WiDr tumor cells stop growing in the presence of IFN-γ and soluble LT-α1/β2 ligand. Control antibodies (IgG1) have no effect on this growth inhibition. In contrast, the anti-LT-β-R mAb BDA8 blocks the ability of soluble LT-α1/β2 ligand to inhibit WiDr cell growth. Thus an antibody directed against human LT-β-R can function as a LT-β-R blocking agent as defined by the present invention.

By testing other antibodies directed against the human LT-β receptor, it is expected that additional anti-LT-β-R antibodies that function as LT-β-R blocking agents in humans can be identified using routine experimentation and the assays described herein.

Source of Anti-Surface LT Ligand Antibodies

Another preferred embodiment of this invention involves compositions and methods which comprise antibodies directed against LT ligand that function as LT-β-R blocking agents. As described above for the anti-LT-β-R Abs, anti-LT ligand antibodies that function as LT-β-R blocking agents can be polyclonal or monoclonal, and can be modified according to routine procedures to modulate their antigen binding properties and their immunogenicity.

The anti-LT antibodies of this invention can be raised against either one of the two LT subunits individually, including soluble, mutant, altered and chimeric forms of the LT subunit. If LT subunits are used as the antigen, preferably they are LT-β subunits. If LT-α subunits are used, it is preferred that the resulting anti-LT-α antibodies bind to surface LT ligand and do not cross-react with secreted LT-α or modulate TNF-R activity (according to the assays described in Example 3).

Alternatively, antibodies directed against a homomeric (LT-β) or a heteromeric (LT-α/β) complex comprising one or more LT subunits can be raised and screened for activity as LT-β-R blocking agents. Preferably, LT-α1/β2 complexes are used as the antigen. As discussed above, it is preferred that the resulting anti-LT-α1/β2 antibodies bind to surface LT ligand without binding to secreted LT-α and without affecting TNF-R activity.

The production of polyclonal anti-human LT-α antibodies, is described in applicants' co-pending application (WO 94/13808). Monoclonal anti-LT-α and anti-LT-β antibodies have also been described (Browning et al., *J. Immunol.*, 154, pp. 33-46 (1995)).

Mouse anti-human LT-β mAbs were prepared as described in Example 6. A hybridoma cell line (B9.C9.1) which produces the mouse anti-human LT-β-R mAb B9 was deposited on Jul. 21, 1995 with the American Type Culture Collection (ATCC) (Rockville, Md.) according to the provisions of the Budapest Treaty, and was assigned the ATCC accession number HB11962.

Monoclonal hamster anti-mouse LT-α/β antibodies were prepared as described in Example 7. A hybridoma cell line (BB.F6.1) which produces the hamster anti-mouse LT-α/β mAb BB.F6 was deposited on Jul. 21, 1995 with the American Type Culture Collection (ATCC) (Rockville, Md.) according to the provisions of the Budapest Treaty, and was assigned the ATCC accession number HB11963.

All restrictions on the availability to the public of the above ATCC deposits will be irrevocably removed upon the granting of a patent on this application.

Anti-LT Ligand Antibodies as LT-β-R Blocking Agents

A fluorescence-activated cell sorting (FACS) assay was developed to screen for antibodies directed against LT subunits and LT complexes that can act as LT-β-R blocking agents (Examples 6 and 7). In this assay, soluble human LT-β-R-Fc fusion protein is added to PMA-activated II-23 cells—which express surface LT complexes (Browning et al., *J. Immunol.*, 154, pp. 33-46 (1995))—in the presence of increasing amounts of the test antibody. An antibody that can inhibit LT-β receptor-ligand interaction by at least 20% is selected as a LT-β-R blocking agent.

Figure 4:
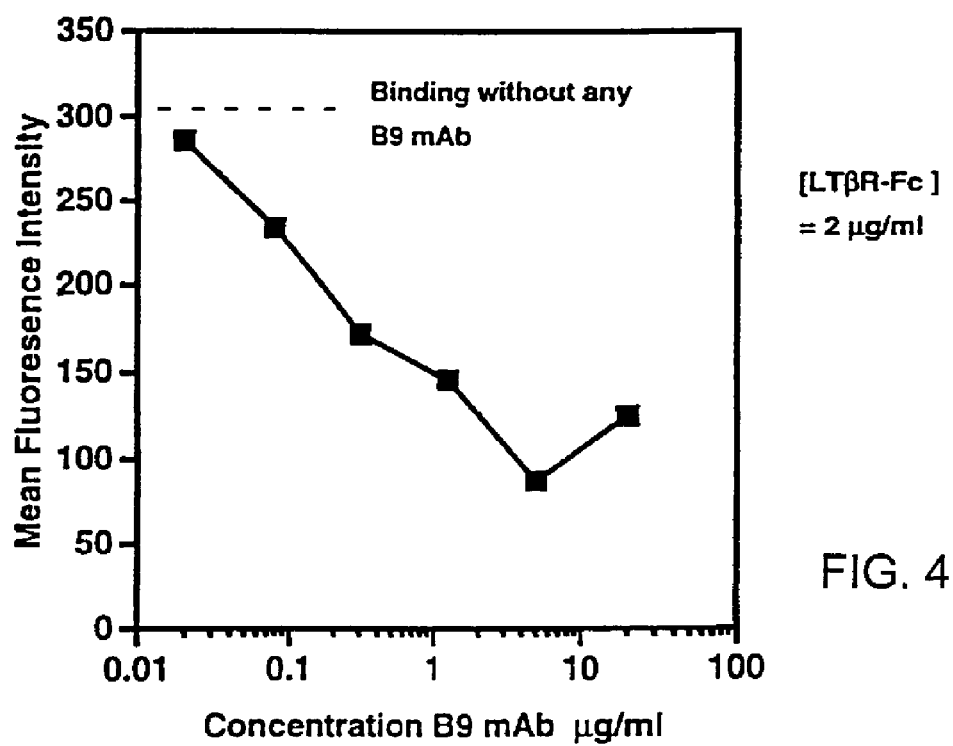
FIG. 4. An antibody directed against human LT-β (B9 mAb) blocks the interaction between cell surface LT-α/β ligand and soluble LT-β receptor (hLT-β-R-Fc; 2 µg/ml). Surface bound LT-β-R-Fc was detected using phycoerythrin-labelled donkey anti-human IgG and FACS analysis. The mean fluorescence intensity of the resultant peak is plotted as channel number. Dotted line shows the mean fluorescence intensity corresponding to the amount of receptor bound in the absence of the B9 mAb.

The results of this assay performed to test the mouse anti-human LT-β mAb B9 are shown in FIG. 4. FIG. 4 shows that anti-LT-β mAb B9 can selectively block the binding of soluble LT-β-R-Fc fusion proteins to surface LT ligands induced on activated cells. These results confirm that antibodies directed against a LT ligand subunit will function as an LT-β-R blocking agent.

The FACS assay described above was also used to test mAbs raised in hamster against a soluble mouse LT-α/β complex (Example 7). The results of this assay performed to test the hamster anti-mouse LT-α/β mAb BB.F6 are shown in Table 2 (Example 7). Table 2 shows that anti-LT-α/β mAb BB.F6 can effectively block the binding of soluble mLT-β-R-Fc fusion proteins (Example 2) to surface LT ligands expressed on a murine T cell hybridoma and is thus a LT-β-R blocking agent according to this invention.

Using a LT-α/β complex rather than a LT subunit as an antigen to immunize an animal may lead to more efficient immunization, or may result in antibodies having higher affinities for surface LT ligand. It is conceivable that by immunizing with the LT-α/β complex, antibodies which recognize amino acid residues on both the LT-α and the LT-β subunits (e.g., residues that form an LT-α/β cleft) can be isolated. By testing antibodies directed against human LT-α/β heteromeric complexes, it is expected that additional anti-LT antibodies that function as LT-β-R blocking agents in humans can be identified using routine experimentation and the assays described herein.

LT-β-R Blocking Agents inhibit Th1 Cell-Mediated Contact Hypersensitivity in Mouse The LT-β-R blocking agents of this invention can inhibit Th1 cell-mediated immune responses. One such Th1-mediated response is delayed type hypersensitivity (DTH; Cher and Mosmann, *J. Immunol.*, 138, pp. 3688-94 (1987); see also I. Roitt et al., Immunology, pp. 22.1-22.12, Mosby-Year Book Europe Ltd., 3d ed. (1993) for a general discussion). DTH is evoked when antigen-sensitized Th1 cells secrete cytokines following a secondary contact with the same antigen. The Th1 cytokines attract and activate macrophages that release additional effector molecules which trigger inflammatory reactions.

DTH reactions are classified into three different types: contact hypersensitivity, tuberculin-type hypersensitivity and granulomatous reactions. The three types of hypersensitivity (HS) may be distinguished by the speed and nature of the response to foreign antigen when it is applied directly to or injected beneath the skin of a sensitized subject. The DTH reaction is monitored by measuring the rate and degree to which the skin thickens.

Tuberculin-type HS reactions are skin reactions which occur at the injection site of a foreign antigen from a microorganism to which the subject has been previously exposed (e.g. *mycobacterium tuberculosis* or *M. leprae*). This skin reaction, which is maximal between 48 and 72 hours, is frequently used as the basis for diagnostic sensitivity tests to previously-encountered microorganisms (e.g. the tuberculin skin test). As a tuberculin-type lesion develops, it can become a granulomatous reaction if the antigen persists in the tissue.

Granulomatous reactions are clinically the most serious DTH reactions because they can lead to many of the pathological effects associated with Th1 cell-mediated diseases. Granulomatous reactions occur when antigens or immune complexes fail to clear from macrophages and continue to stimulate Th1 cytokine secretion. Chronic inflammation and aggregation of activated macrophages at the site of the stimulus characterize granulomatous reactions.

A core of epithelial cells and macrophages, which can also be surrounded by lymphocytes and fibrotic depositions, form a hardened structure called a granuloma. Sometimes there is extensive cell death in the core of the granuloma (e.g. in tuberculosis-affected lung tissue). Hardening in the target tissue of a granulomatous reaction occurs in about 4 weeks.

Agents which afflict the frequency of granuloma formation can be identified using schistosome-infected mice (Amiri et al., *Nature*, 356, pp. 604-607 (1992)). Schistosome worms (blood flukes) can cause a parasitic disease leading to granuloma formation around the schistosome eggs deposited in portal venules of the infected liver. Agents that inhibit this Th1 cell-mediated DTH response may decrease the size of the granuloma, or the frequency or rate of granuloma formation in schistosome-infected mouse livers. Cellular reaction to the schistosome eggs can be assessed by quantitating the number and size of granulomas formed in mice treated with increasing concentrations of a putative LT-β-R blocking agent over time.

Contact hypersensitivity (CHS) is a class of DTH in which skin is the target organ. In CHS, an inflammatory response is caused by locally applying a reactive hapten onto the skin. Allergens generally comprise at least one hapten molecule, which is usually too small to be antigenic on its own. The hapten penetrates the epidermis and reacts with a normal protein under the skin to produce a novel antigenic complex. Re-exposure of a sensitized subject to the hapten triggers the DTH response. The hapten-carrier protein conjugate, in combination with antigen presenting cells, activates effector mechanisms that trigger the release of cytokines (including IL-2, IL-3, IFN-γ and GM-CSF). The cascade of released cytokines causes CD4+ T cells to proliferate, the expression patterns of various cell surface adhesion molecules to change, and the attraction of T cells and macrophages to the skin at the site of inflammation. The cytokine cascade and resulting vasodilation, cellular infiltration and edema of the dermis and epidermis leads to swelling and inflammation of the target tissue, which accounts for the measurable skin thickening in response to DTH reactions.

The degree to which a particular hapten can sensitize an individual depends on a variety of factors. These factors include how well the hapten can penetrate the skin and react with a host carrier protein to form a conjugate. One hapten that sensitizes nearly all individuals is 2,4-dinitro-fluorobenzene (DNFB).

The skin CHS response to a hapten such as DNFB is a classic animal model for cell-mediated immunity. Localization of this CHS response to the ear of a sensitized mouse allows easy, accurate and reproducible quantitation of this cell-mediated immune response in vivo by measuring ear thickness. The details of the murine CHS reaction and the histopathology of the DNFB-induced inflammatory response have been reported (Chisholm et al., *Eur. J. Immunol.*, 23, pp. 682-688 (1993)).

The ability of DNFB to induce a contact hypersensitivity response in most individuals can be used to identify agents that reduce or eliminate the inflammatory responses associated with Th1 cell-mediated DTH reactions. A soluble murine LT-β-R-Fc fusion protein effectively inhibits DNFB-induced contact hypersensitivity responses in mice (Example 8). Mice were initially sensitized by applying DNFB onto the bottom of each hind foot on two consecutive days. Five days after the initial sensitization, a sub-irritant dose of DNFB in carrier solution was applied to the surfaces of the left ear. Carrier solution alone was applied to the right ear as a control.

Increasing concentrations of the LT-β-R blocking agent mLT-β-R-Fc (Example 2) were then injected intravenously into the mice (Example 8). Injections of PBS buffer alone, or of a human IgG fusion protein (LFA3-Fc) served as negative controls, and injection of an anti-VLA4-specific mAb (PS/2 mAb) known to inhibit CHS served as a positive control. Twenty-four hours after challenge, the thickness of each ear (DNFB-challenged and -unchallenged) was measured. Inhibition of the ear swelling response by the LT-β-R blocking agent was judged by comparison of treated groups with their negative control group.

Figure 5:
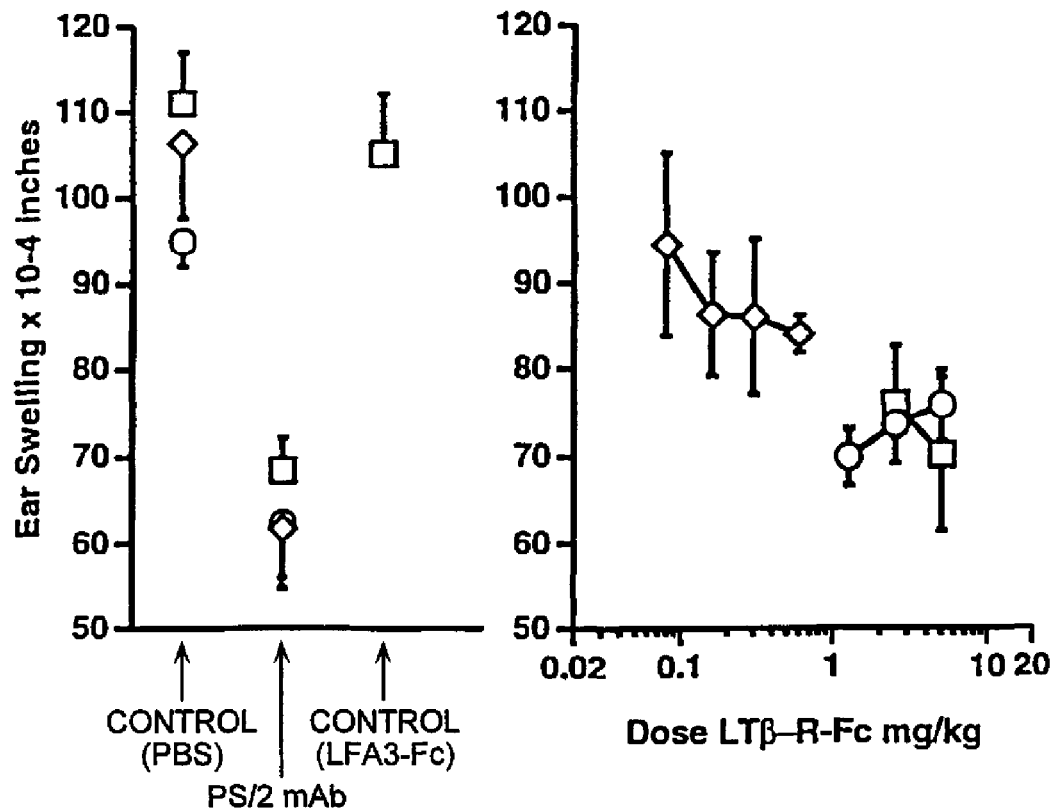
FIG. 5. The effects of a LT-β-R blocking agent (mLT-β-R-Fc) on ear swelling in a mouse contact delayed type hypersensitivity model (DTH). The graph shows the increase in ear thickness measured 24 hours following 0.2% DNFB antigen challenge onto the ears of sensitized mice. Each symbol represents a separate experiment. All experiments utilized 7-8 animals per point except those demarcated with a diamond, which used only 4 animals per point. Mice treated with buffer (PBS) and with 20 mg/kg of a control IgG fusion protein (LFA3-Fc) served as negative controls. Mice treated with 8 mg/kg of an anti-vLA4 mAb (PS/2 mAb), which inhibits contact DTH ear swelling, served as positive controls.

FIG. 5 shows that mLT-β-R-Fc causes a significant reduction in the ear swelling response of DNFB-treated mice compared to uninhibited DNFB-treated control animals (PBS and LFA3-Fc). Soluble LT-β-R can block this CHS reaction as effectively as the inhibitor anti-VLA4-specific mAb (PS/2 mAb), which acts by blocking the influx of T cells into the challenge site (Chisholm et al., *Eur. J. Immunol.*, 23, pp. 682-88 (1993)).

These data show that a soluble LT-β-R fusion protein which acts as a LT-β-R blocking agent in vitro can also effectively inhibit a Th1 cell-mediated immune response when administered to an animal. The LT-β-R blocking agents of this invention identified in vitro can be tested using this ear swelling assay, or other DTH assays such as those described above, to select additional LT-β-R blocking agents that will be useful for reducing the severity of Th1 cell-associated immune responses in vivo.

LT-β-R Blocking Agents Do Not Inhibit a Th2 Cell-Mediated (Humoral) Immunological Response As shown above, the LT-β-R blocking agents of this invention can inhibit a Th1 cell-mediated effector mechanism such as contact delayed type hypersensitivity (FIG. 5). This Th1 cell-mediated response is inhibited without significantly affecting Th2 cell-dependent responses. The differential effect of LT-β-R blocking agents on Th1 cell-mediated immune responses was shown by monitoring a Th2-cell dependent immune response—such as a primary antibody response and isotype switching—in the presence of an LT-β-R blocking agent.

Mice were injected five times over the course of a ten day period with either soluble LT-β-R fusion protein (mLT-β-R-Fc; Example 2) or control IgG fusion protein (LFA3-Fc), or were left untreated. After the second injection, all mice were injected in the base of the tail with 100 μl of complete Freund's adjuvant containing 100 μg of ovalbumin. After 11 days, primary serum anti-ovalbumin-specific antibody titers were analyzed using an ELISA specific for IgG1, IgG2a and IgM isotypes.

Figure 6:
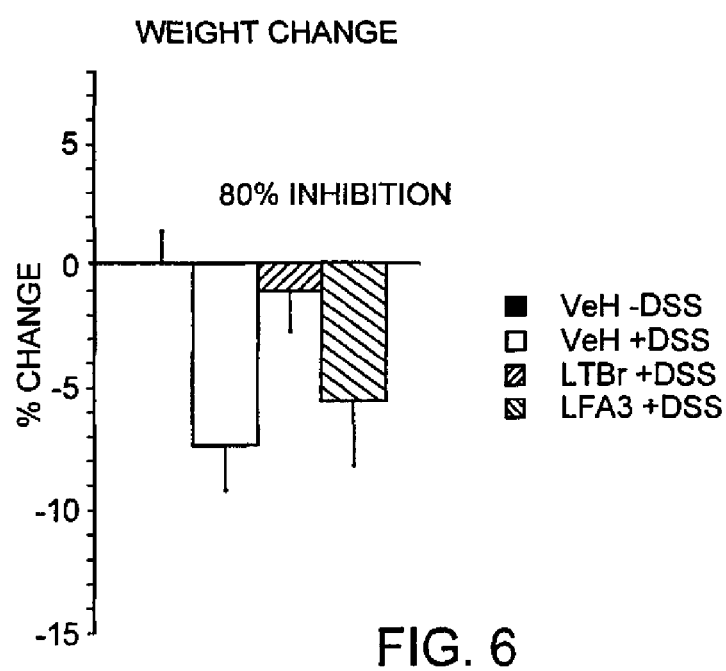
FIG. 6 is a graph of the weight change observed in mice 14 days after treatment with mLT-βR-lg and hLFA3-lg fusion proteins.

FIG. 6 shows the effect of the mouse LT-β-R blocking agent mLT-β-R-Fc on serum anti-ovalbumin antibody production in mice immunized with ovalbumin (Example 9). Administering the LT-β-R blocking agent does not significantly affect primary antibody titers following ovalbumin immunization. By comparison, interfering with CD40 ligand-induced CD40 receptor signalling completely blocks the antigen-specific IgG response in mice (Renshaw et al., *J. Exp. Med.*, 180, pp. 1889-1900 (1994)). CD40 is another ligand/receptor pair in the TNF family.

Figure 7:
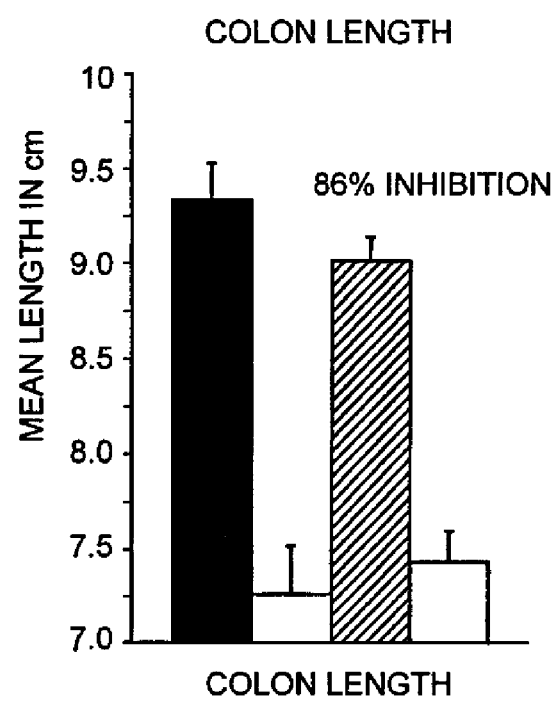
FIG. 7 is a graph of the change in colon length observed in mice 14 days after treatment with mLT-βR-lg and hLFA3-lg fusion proteins.

Total immunoglobulin production and maturation is clearly Th2 cell-dependent. However, there is also evidence that the Th1 cytokine IFN-γ participates but is not absolutely required for the switch to the IgG2a subclass (Huang et al., *Science*, 259, pp. 1742-45 (1993)). The LT-β-R blocking agent mLT-β-R-Fc did not inhibit the IgG2a switch in these experiments. It is possible that the LT-β-R blocking agents of this invention do not block this humoral aspect of a Th1 cell-mediated response. In addition, the proliferatory responses of lymphocytes from the
mLT-β-R-Fc-treated mice were not decreased (Example 10; FIG. 7)

These experiments indicate that a therapy based on administering the LT-β-R blocking agents of this invention will not adversely affect Th2 dependent antibody production functions of an immune response. The normal pattern of antibody response illustrated in FIG. 6 also indicates that an intensive treatment with soluble mLT-β-R-Fc was not toxic to the mice, further indicating the useful therapeutic nature of the compositions and methods set forth in this invention.

T Helper Cell-Mediated Diseases

Many organ-specific autoimmune conditions appear to involve pathological Th1 response. These data have been reviewed (Modlin and Nutman, *Current Opinion in Immunol.*, 5, pp. 511-17 (1993); Romagnani et al., *Ann. Rev. Immunol.*, 12, pp. 227-57 (1994)). These organ-specific autoimmune conditions include: multiple sclerosis, insulin-dependent diabetes, sympathetic ophthalmia, uveitis and psoriasis.

Insulin-dependent diabetes mellitus is an autoimmune disease in which the insulin-producing beta pancreatic cells are destroyed by leukocytes infiltrating into the islets of Langerhans. Diabetes can be rapidly induced in neonatal nonobese diabetic (NOD) mice by transferring activated prediabetic splenocytes. Recently, Th1- or Th2-like cells, otherwise genetically similar, were transferred into neonatal NOD mice. Only the Th1 cells rapidly induced diabetes—and in almost all recipients (Katz et al., *Science*, 268, pp. 1185-88 (1995)). This indicates that the LT-β-R blocking agents of this invention—which can inhibit the effects of a Th1 cell-mediated immune response in vivo—will be useful for treating or preventing insulin-dependent diabetes.

Several systemic autoimmune diseases, including various arthritides, are Th1 cell-associated. Rheumatoid arthritis and Sjogren's syndrome both appear to involve Th0 and Th1 cells. In contrast, systemic lupus erythematosus (SLE) appears to have an aberrant Th0/Th2 dominant response.

Some chronic inflammatory diseases also appear to have an aberrant Th1 type response, including inflammatory bowel disease, sarcoidosis of the lung and allograft rejection. Inflammatory bowel disease (IBD) in humans encompasses at least two categories, ulcerative colitis and Crohn's disease. Both disorders are believed to result from immunopathologic autoimmune like disorders. In some mouse models of IBD, it is clear that some agents that block Th1 responses can block the development or course of the disease (F. Powrie et al, Immunity 1:553 1994). It is possible that inhibition of the Th1 component of the immune response would have beneficial effects in human IBD. Many models of IBD have been described and have been reviewed (C. Elson et al, Gastroenterology 109:1344 1995). There are at least three groups of models, chemically induced, polymer/microbial-induced and immunological types using mutant mice.

In one commonly used polymer/microbial-induced model, dextran sulphate solution is introduced into the drinking water of mice and upon ingestion, the epithelial lining of the gut is irritated leading to a profound immune response to the damage. The animals develop colitis which is manifested as diarrhea, blood in the stool, loss of body weight and a shortening of the colon length due to expansion of the colon wall. This model induces a left-sided colitis and epithelial dysplasia which can lead to cancer which are features of ulcerative colitis.

A second model consists of transplanting a selected set of CD4 T cells into a acid mouse, i.e. a mouse lacking T and B cells (F. Powrie et al International Immunology 5:1461-1471 1993; Morrissey et al, J. Exp. Med. 178:237 1993). As the selected cells, called CD45RB$^{hi}$ cells expand and reconstitute the scid mouse, the normal mechanisms preventing the appearance of autoreactive T cells are dysfunctional and autoreactive cells develop. In rats, cells reactive with many organs are observed whereas, in the mouse, the reactivity occurs primarily in the bowel. Agents which either alter the way the autoreactive cells expand and develop or agents which can block the ability of the cells to attack the bowel will have efficacy in this model. Moreover, as this model at least partially mimics the pathological development of autoreactive immune system cells, treatments that block this model may actually have disease modifying behavior in humans. In this model, antibodies to TNF can block disease (P. Powrie et al Immunity 1, 552 1994) and these antibodies have been found to be efficacious in the treatment of human disease (H. M. van Dullemen et al. Gastroenterology 109:109 1995). Thus, this model can forecast which agents may be therapeutically useful in IBD. Moreover, as the CD45RB model is an example of a Th1 mediated disease process and indeed in rats, the model leads to disease in many organs, the efficacy of LTβR-Ig in this system indicates that LTβR-Ig or other means of blocking the LTβR interactions with its ligand may be beneficial in a wide range of related immunological diseases.

In general, the exact contribution of auto-antibodies versus specific T cells has not been delineated in these autoimmune diseases. Cellular responses may make major contributions to pathogenicity in those systemic autoimmune diseases currently thought to be primarily antibody driven, e.g. the various arthritides.

The normal immune response to some pathogenic infectious agents also elicits a Th1 response that can become excessive and present itself as a medical problem. Examples of granulomatous reactions (a class of DTH response described above) that lead to severe medical problems include leprosy, granuloma formation in the lungs of tuberculosis patients, sarcoidosis and schistosomiasis (Roitt et al., Immunology, pp. 22.5-6 (Mosby-Year Book Europe Ltd., 3d ed. 1993). Psoriasis is also likely to be mediated by Th1 cells.

Cytolytic T cells, i.e. CTLs (CD8 positive T cells) may also subdivide into Th2- and Th2-like populations. Therefore it is possible that much of what is known regarding the Th groups will also apply to CD8+ cells, which are primarily involved in anti-viral and grafted tissue rejection responses.

Treatments Using LT-β-R Blocking Agents

The compositions of this invention will be administered at an effective dose to treat the particular clinical condition addressed. Determination of a preferred pharmaceutical formulation and a therapeutically efficient dose regiment for a given application is well within the skill of the art taking into consideration, for example, the condition and weight of the patient, the extent of desired treatment and the tolerance of the patient for the treatment. Doses of about 1 mg/kg of a soluble LT-β-R are expected to be suitable starting points for optimizing treatment doses.

Determination of a therapeutically effective dose can also be assessed by performing in vitro experiments that measure the concentration of the LT-β-R blocking agent required to coat target cells (LT-β-R or LT ligand-positive cells depending on the blocking agent) for 1 to 14 days. The receptor-ligand binding assays described herein can be used to monitor the cell coating reaction. LT-β-R or LT ligand-positive cells can be separated from activated lymphocyte populations using FACS. Based on the results of these in vitro binding assays, a range of suitable LT-β-R blocking agent concentrations can be selected to test in animals according to the assays described herein.

Administration of the soluble LT-β-R molecules, anti-LT ligand and anti-LT-β-R Abs of this invention, alone or in combination, including isolated and purified forms of the antibodies or complexes, their salts or pharmaceutically acceptable derivatives thereof, may be accomplished using any of the conventionally accepted modes of administration of agents which exhibit immunosuppressive activity.

The pharmaceutical compositions used in these therapies may also be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The soluble LT-β-R molecules, anti-LT ligand and anti-LT-β-R Abs of this invention may, for example, be placed into sterile, isotonic formulations with or without cofactors which stimulate uptake or stability. The formulation is preferably liquid, or may be lyophilized powder. For example, the soluble LT-β-R molecules, anti-LT ligand and anti-LT-β-R Abs of this invention may be diluted with a formulation buffer comprising 5.0 mg/ml citric acid monohydrate, 2.7 mg/ml trisodium citrate, 41 mg/ma mannitol, 1 mg/ml glycine and 1 mg/ma polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773, 319; EP 58,481), copolymers of L-glutamic acid and ethyl-L-glutamate (Sidman et al., *Biopolymers*, 22, pp. 547-56 (1985)); poly(2-hydroxyethyl-methacrylate) or ethylene vinyl acetate (Langer et al., *J. Biomed. Mater. Res.*, 15, pp. 167-277 (1981); Langer, *Chem. Tech.*, 12, pp. 98-105 (1982)).

Liposomes containing soluble LT-β-R molecules, anti-LT ligand and anti-LT-β-R Abs of this invention, alone or in combination, can be prepared, by well-known methods (See, e.g. DE 3,218,121; Epstein et al., *Proc. Natl. Acad. Sci. U.S.A.*, 82, pp. 3688-92 (1985); Hwang et al., *Proc. Natl. Acad. Sci. U.S.A.*, 77, pp. 4030-34 (1980); U.S. Pat. Nos. 4,485,045 and 4,544,545). Ordinarily the liposomes are of the small (about 200-800 Angstroms) unilamellar type in which the lipid content is greater than about 30 mol. % cholesterol. The proportion of cholesterol is selected to control the optimal rate of soluble LT-β-R molecule, anti-LT ligand and anti-LT-β-R Ab release.

The soluble LT-β-R molecules, anti-LT ligand and anti-LT-β-R Abs of this invention may also be attached to liposomes containing other LT-β-R blocking agents, immunosuppressive agents or cytokines to modulate the LT-β-R blocking activity. Attachment of LT-β-R molecules, anti-LT ligand and anti-LT-β-R Abs to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., *J. Cell. Biochem. Abst. Suppl.* 16E 77 (1992)).

Advantages of Therapeutic Compositions Comprising LT-β-R Blocking Agents

The LT-β-R blocking agents of this invention are capable of selectively inhibiting Th1 and not Th2 cell-dependent immune effector mechanisms. LT-β-R blocking agents will be useful in treating conditions that are exacerbated by the activities of Th1-type cytokines (e.g., IL-2 and IFN-γ). Because Th1 cytokines can inhibit Th2 cell-dependent responses, LT-β-R blocking agents may also indirectly stimulate certain Th2 cell-dependent responses that are normally inhibited by Th1-induced cytokine cascades.

The ability to selectively suppress Th1 (or indirectly stimulate Th2) cell responses will be useful for treating abnormalities in diverse cell-mediated immune responses including various autoimmune and chronic inflammatory conditions, antigen tolerance, and cellular rejection of tissue grafts and organ transplants.

As discussed above, treatment of Th1 cell-based immunological conditions generally employs immunomodulatory and immunosuppressive agents which have pleiotropic effects on a wide variety of cell types and immunological responses. These non-specific immunosuppressive agents are generally required in high and often cytotoxic doses that cause adverse side effects.

The ability to shift the character of an immunological response is supported in the recent study of mouse diabetes discussed above (Katz et al., *Science,* 268, pp. 1185-88 (1995)), and in an allogeneic transplant model (Sayegh et al., *J. Exp. Med.,* 181, pp. 1869-74 (1995)). In the latter study, a fusion protein that blocks the CD28-B7 T cell costimulatory pathway was shown to induce renal graft tolerance. The tolerance correlated with a decrease in Th1 cytokines and an increase in Th2 cytokines in vivo. These data indicate that the LT-β-R blocking agents of this invention will be useful in suppressing cellular rejection of tissue grafts and organ transplants by inhibiting Th1 cell-mediated cytokine release.

The LT-β-R blocking agents of the compositions and methods of this invention can be modified to obtain a desirable level of LT-β-R signalling depending on the condition, disorder or disease being treated. It is envisioned that the desired level of LT-β-R signalling can be fine-tuned by manipulating the concentration and the affinities of the LT-β-R blocking agents for their respective molecular targets.

For example, in one embodiment of this invention, compositions comprising soluble LT-β-R molecules are administered to a subject. The soluble LT-S receptor can effectively compete with cell surface LT-β receptors for binding surface LT ligands. The ability to compete with surface LT ligands depends on the relative concentrations of the soluble and the cell surface LT-β-R molecules, and on their relative affinities for ligand binding.

Soluble LT-β-R molecules harboring mutations that increase or decrease the binding affinity of that mutant soluble LT-β-R with surface LT ligand can be made using standard recombinant DNA techniques well known to those of skill in the art. Large numbers of molecules with site-directed or random mutations can be tested for their ability to act as LT-β-R blocking agents using routine experimentation and the techniques described herein.

Similarly, in another embodiment of this invention, antibodies directed against either the LT-β receptor or one or more of the LT ligand subunits function as LT-β-R blocking agents. The ability for these antibodies to block LT-β receptor signalling can be modified by mutation, chemical modification or by other methods that can vary the effective concentration or activity of the antibody delivered to the subject.

The ability to diminish LT-β-R signalling without completely inhibiting it may be important for establishing or maintaining reduced levels of LT-β-R signalling that support normal immune function while inhibiting Th1-cell mediated responses which are exaggerated or abnormal.

Disruption of the LT-α gene in a mouse leads to aberrant peripheral lymphoid organ development (De Togni et al., *Science,* 264, pp. 703-7 (1994)). Such mice lacked lymph nodes and their spleens lacked the usually clear demarcation between T and B cell-rich regions in the follicles. We believe that this phenotype is associated with loss of surface LT-induced LT-β-R signalling because similar phenotypes have not been observed by modulating TNF-R activity. The ability to selectively or to partially block the LT-β-R pathway may thus be useful in treating abnormal lymphoid organ development associated with mis- or over-expression of signalling by the LT-β-R pathway.

Some Th1-associated reactions are critical components of a number of cell-mediated immune responses (Romagnani, S., *Ann. Rev. Immunol.,* 12, pp. 227-57 (1994)), and absolute inhibition of Th1 cell activity may not be desirable in certain circumstances. For example, a mouse can effectively resist a parasitic infection when a good Th1 response can be mounted. Infectious agents such as *Listeria* and *Toxoplasma* also elicit strong Th1-type responses. In humans, *mycrobacterium tuberculosis* responses appear to be Th1-based. Leishmaniasis pathogenicity correlates with responses similar to the Th1 responses characterized in mouse (Reed and Scott, *Current Opinion in Immunol.* 5, pp. 524-31 (1993)).

The ability to influence the level of Th1 inhibition by blocking LT-β-R signalling may be important in maximizing the beneficial results which can be achieved by treatments with the LT-β-R blocking agents of this invention.

The following are examples which illustrate the soluble LT-β receptors, anti-LT ligand and anti-LT-β-R antibodies of this invention and the methods used to characterize them. These examples should not be construed as limiting: the examples are included for purposes of illustration and the present invention is limited only by the claims.

Example 1

Preparation of Soluble Human LT-β Receptors as Immunoglobulin Fc Fusion Proteins The sequence of a human cDNA clone isolated from a library of human 12p transcribed sequences derived from a somatic cell hybrid (Baens et al., *Genomics,* 16, pp. 214-18 (1993)) was entered into GenBank and was later identified as the sequence which encodes human LT-β-R. The sequence of this full-length human LT-β-R cDNA clone has been available since 1992 as GenBank entry L04270.

The extracellular domain of LT-β-R up to the transmembrane region (FIG. 1) was amplified by PCR from a cDNA clone using primers that incorporated NotI and SalI restriction enzyme sites on the 5' and 3' ends, respectively (Browning et al., *J. Immunol.,* 154, pp. 33-46 (1995)). The amplified product was cut with NotI and SalI, purified and ligated into a NotI-linearized vector pMDR901 along with a SalI-NotI fragment encoding the Fc region of human IgG1. The resultant vector contained the dihydrofolate reductase gene and the LT-β-R-Fc fusion protein driven by separate promoters.

The vector was electroporated into CHO dhfr⁻ cells and methotrexate-resistant clones were isolated as per standard procedures. The LT-β-R-Fc was secreted into the medium and an ELISA assay was used to select for cell lines producing the highest level of the receptor fusion protein. A high-producing cell line was grown to large numbers and the conditioned medium collected. The pure LT-β receptor fusion protein was isolated by Protein A Sepharose Fast Flow affinity chromatography (Pharmacia).

Example 2

Preparation of Soluble Marine LT-β Receptors as Immunoglobulin Fc Fusion Proteins A complete cDNA clone of the mLT-β-R was prepared by ligating a 5' NotI/ApaLI and 3' ApaLI/NotI fragments from two partial cDNA, isolates into the NotI site of pCDNA3 (InVitrogen, San Diego, Calif.). The sequence of this cDNA clone is accessible as GenBank entry U29173. No coding sequence differences were noted when compared with another sequence entry for mLT-β-R found in GenBank entry L38423.

A soluble mLT-β-R (hIgG1) fusion protein was prepared by PCR amplification of the full length mLT-β-R cDNA clone as a template and the primers 5'AACTGCAGCGGCCGC-CATGCGCCTGCCC 3' and 5'GACTTTGTCGACCAT-TGCTCCTGGCTCTGGGGG 3'. The amplified product was purified and cut with NotI and SalI and ligated with a SalI/NotI human IgG1 Fc fragment into NotI-linearized and phosphatase-treated SAB132 to form JLB 122. For stable expression, the NotI cassette containing the mLT-β-R-Fc fragment was transferred into the NotI site of pMDR901 forming PSH001 and the vector was transfected into CHO cells as described (Browning et al., *J. Immunol.*, 154, pp. 33-46 (1995)). Cell clones secreting mLT-β-R-Fc were identified by ELISA analysis. The purified receptor fusion protein was isolated from CHO cell supernatants by Protein A Sepharose Fast Flow chromatography (Pharmacia).

Example 3

Use of Soluble Human LT-β-R-Fc to Block LT-β Receptor-Ligand Interactions

Soluble hLT-β-R-Fc was tested for its ability to block LT ligand binding to the LT-β receptor in the tumor cell cytotoxicity assay described above. In this assay, a soluble form of the LT ligand (hLT-α1/β2), which activates LT-β-R signalling, is used to kill human tumor cells. Inhibitors of LT-β-R signalling can reduce LT-β-R-Induced tumor cell cytotoxicity.

Soluble LT-α1/β2 ligands comprise truncated or modified LT-β subunits lacking a functional transmembrane domain. Soluble LT-α1/β2 ligands bind to and stimulate LT-β-R signalling as well as surface forms of LT ligand (Browning et al., *J. Immunol.*, 154, pp. 33-46 (1995)).

Serial dilutions of hLT-α1/β2, hTNF or hLT-α were prepared in 0.05 ml in 96 well plates and 5000 trypsinized HT29 cells (ATCC) added in 0.05 ml media containing 80 U/ml (antiviral units) of hu-IFN-γ. After 4 days, mitochondrial reduction of the dye MTT was measured as follows: 10 μl of MTT was added and after 3 hours, the reduced dye dissolved with 0.09 ml of isopropanol with 10 mM HCl, and the O.D. measured at 550 nm. Soluble receptor forms or pure human IgG were added in 10 μl prior to the addition of the cells to give a final concentration of 5 μg/ml.

Table 1 compares the ability of hLT-β-R-Fc and p55-TNF-R-Fc chimeras (with human IgG as a control) to block the inhibitory effects of various soluble TNF and LT ligands on HT29 tumor cell growth.

TABLE I

Ability of LT-β-R and p55-TNF-R Immunoglobulin Fusion Proteins to Block the Inhibitory Effects of Various TNF and LT Ligands on HT29 Growth
Concentration of Cytotoxic Agent (ng/ml)
Resulting in 50% Growth Inhibition

| Cytotoxic Agent | In the Presence of[a] | | |
|---|---|---|---|
| | hu-IgG control | p55-TNF-R-Fc | LT-β-R-Fc |
| TNF | 0.08 | >10[b] | 0.08 |
| LT-α | 3 | >1000 | 3 |
| LT-α1/β2 | 5 | 5 | >200 |

[a]Each cytotoxic agent was pre-mixed with the Ig fusion proteins for 10 minutes prior to addition to the cells. The final concentration of fusion protein was 5 μg/ml.
[b]Higher concentrations were not tested.

The data in Table 1 indicate that the soluble human LT-β-R fusion protein (hLT-β-R-Fc) can effectively block the interaction between LT ligand (LT-α1/β2) and cell surface LT-β receptors and is thus a LT-β-R blocking agent according to this invention.

As expected, the soluble TNF-R fusion protein (p55-TNF-R-Fc) completely blocked TNF-induced growth inhibition by binding to TNF and preventing its interaction with surface TNF receptors. This soluble TNF receptor had no effect on LT ligand-mediated anti-proliferative effects. In contrast, the LT-β-R-Fc blocked LT ligand-induced cytotoxic effects but not those of TNF or LT-α. Thus soluble human LT-β-R fusion proteins do not interfere with TNF-R activation by TNF and LT-α ligands.

Example 4

Use of Soluble Murine LT-β-R-Fc to Block Mouse LT-β Receptor-Ligand Interactions A soluble murine LT-β receptor coupled to a human IgG1 Fc domain (mLT-β-R-Fc; see Example 2) was tested for its ability to block LT-β receptor-ligand interaction in mouse using a cytotoxicity assay on mouse cells (FIG. 2). The cytotoxicity assay was performed on WEHI 164 cells using essentially the same procedure as was used in the HT29 cell assay described in Example 3 (see also Browning and Ribolini, *J. Immunol.*, 143, pp. 1859-67 (1989)).

FIG. 2 shows the effects of mLT-β-R-Fc on ligand-induced LT-β-R signalling in mouse WEHI 164 cells. As this assay indicates, WEHI 164 cells are killed by treating them with LT-α/β ligand at concentrations ranging from about 1 to 100 ng/ml. Soluble mLT-β-R-Fc (10 μ/ml) blocks the LT ligand-activated cell death. Adding a soluble mouse p 5-TNF-R-Fc fusion protein or IgG control antibodies (each at 10 μ/ml) had little or no effect on blocking cell death. These data show that the mLT-β-R-Fc fusion protein can effectively compete with surface LT-β-R molecules for LT ligand binding. These data also show that LT-α/β-induced cytotoxicity is LT-β-R-mediated and can be inhibited by soluble mLT-β-R-Fc, which acts as a LT-II-R blocking agent according to the present invention.

Example 5

Use of Anti-Human LT-β-R Antibodies to Block LT-β Receptor-Ligand Interactions

Mouse monoclonal antibodies (mAbs) directed against the human LT-β receptor were prepared by intraperitoneal immunization of RBF mice repetitively with a CHO cell-derived hLT-β-R-Fc fusion protein attached to Protein A Sepharose beads in the absence of adjuvant. Animals were finally boosted with soluble hLT-β-R-Fc, both i.p. and i.v., spleen cells were fused via classical protocols and hybridoma supernatants were screened by ELISA (Ling et al., *J. Interferon and Cytokine Res.*, 15, pp. 53-59 (1995)). Hybridoma supernatants were screened further for their ability to block binding of activated II-23 hybridoma cells—which express surface LT-α1/β2—to LT-β-R-Fc coated plates in a cell panning assay. Pure mAbs were prepared by Protein A Sepharose purification (Pharmacia) of IgG from culture supernatants.

To determine whether an anti-LT-β receptor mAb could block LT-β-R signalling initiated by the binding of soluble LT, a tumor cell cytotoxicity assay was performed using WiDr human carcinoma cells. In the cytotoxicity assays, serial dilutions of LT-α1/β2 were prepared in 0.05 ml in 96 well plates and 10 μl of a 100 μg/ml solution containing either control mouse IgG1 mAb or the anti-LT-β receptor mAb was added. 5000 trypsinized WiDr cells (ATCC) were then added to each well in 0.05 ml of media containing 50 p/ml (antiviral units) of hu-IFN-γ. After 4 days, mitochondrial reduction of the dye MTT was measured as follows: 10 μl of MTT was added and after 3 hours, the reduced dye dissolved with 0.09 ml of isopropanol with 10 mM HCl, and the O.D. measured at 550 nm. The amount of purple color is proportional to the amount of cell growth.

FIG. 3 shows that the anti-LT-β-R mAb BDA8 acts as a LT-β-R blocking agent according to this invention. Human WiDr carcinoma cells stop growing in the presence of IFN-γ and soluble LT-α1/β2 ligand (from about 0.05 to 50 ng/ml). An IgG1 control antibody (10 μg/ml) has no effect on this growth inhibition. In contrast, the anti-LT-β-R mAb BDA8 (10 μg/ml) restores the ability of WiDr cells to grow in the presence of soluble LT-α1/β2 ligand.

Example 6

Use of Anti-Human LT-β Antibodies to Block Receptor-Ligand Interactions

Anti-human LT-β mAbs were prepared by immunizing RBF mice with washed protein A Sepharose-9E10-rLT-β beads containing about 1-2 μg of human recombinant LT-β in CFA, and followed with one boost of the same material in IFA. Eight weeks after the last boost, mice were given i.v. 30 μg of purified soluble rLT-E (acid eluted off the 9E10 resin) and 20 μg of the same soluble material 2 days later. One day after the second i.v. boost, the spleen cells were fused using classical protocols to create mAbs. Hybridoma supernatants were screened directly by ELISA or by FACS staining of PMA-activated II-23 cells. Pure mAbs were prepared by Protein A Sepharose Fast Flow purification of IgG from culture supernatants (Pharmacia).

A FACS assay was used to select antibodies directed against LT-β that can effectively block the binding of soluble LT-α/β ligand to LT-β receptors on the surface of a cell—thus mimicking the interaction between two cells in vivo. In this assay, soluble human LT-β-R-Fc (2 μg/ml) was allowed to bind to surface LT ligand on PMA-activated II-23 cells (Browning et al., *J. Immunol.*, 154, pp. 33-46 (1995)) in the presence of increasing concentrations of the test anti-LT-β mAb (0.02-20 μg/ml). The cells were washed and the bound LT-β-R-Fc was detected by reaction with phycoerythrin-labelled donkey anti-human IgG. The amount of bound fluorescent label was determined by FACS analysis and the mean fluorescence intensity was plotted.

FIG. 4 shows the results of a FACS assay which measured the ability of the anti-LT-β mAb B9 to block LT-β receptor-ligand interaction as described above. This experiment shows that the anti-LT-β mAb B9 (0.02-5 μg/ml) can specifically and effectively compete for cell surface LT ligand binding with soluble LT-β-R fusion protein (2 μg/ml) and thus qualifies as an LT-β-R blocking agent according to this invention.

Example 7

Use of Anti-Mouse LT-α/β Antibodies to Block Receptor-Ligand Interactions

Soluble mouse LT-α/â complexes were prepared as described above for the human soluble LT-α/β complexes. The soluble mouse LT-â subunit was made based on sequence information previously described (Lawton et al., *J. Immunol.* 154, pp. 239-46 (1995)). Soluble murine LT-α/â complexes were expressed using the baculovirus/insect cell expression system and the LT-α/â complexes were isolated by affinity chromatography using human p55 TNF-R and LT-â-R columns essentially as described above for the expression and purification of human LT-α/â complexes. Armenian hamsters were immunized with purified soluble murine LT-α/β complex essentially as described in Example 6. Hamster spleen cells were fused to the mouse P3X hybridoma cell line as described (Sanchez-Madrid et al., *Methods of Enzymology*, 121, pp. 239-44 (1986)). Hybridomas were grouped as anti-mLT-â or anti-mLT-α on the basis of their binding characteristics to either the LT-α/â complex or to LT-α alone, respectively. Hybridoma cells were expanded and the antibodies purified from the culture supernatant using Protein A affinity chromatography (Pharmacia).

To assess whether hamster anti-mouse LT-α and LT-β mAbs could block LT ligand binding to mLT-â-R, we used TIMI-4 cells (ATCC), a murine T cell line that expresses surface LT ligand following PMA activation for 7 hours. Hamster anti-mLT-α or anti-mLT-β mAbs were preincubated with the cells for 30 minutes at 4 C and then washed twice. The washed cells were incubated with 1 μg/ml of mLT-β-R-Fc at 4 C. After 30 minutes, cells were washed free of unbound mLT-β-R-Fc and then incubated for 30 minutes with 10 μg/ml of phycoerythrin-labelled donkey anti-human IgG to detect bound mLT-β-R-Fc. The amount of bound fluorescent label was determined by FACS analysis and the mean fluorescence intensity was calculated.

Using this analysis, it was found that the hamster anti-mLT-â mAb could effectively block soluble LT-β receptor binding to T cell surface LT ligand. The results are shown in Table 2.

TABLE 2

Ability of Anti-mouse LT-β Monoclonal Antibody To Inhibit mLT-β-R-Fc Binding To Murine Surface LT Ligand

| Conc. mAb (μg/ml) | Anti-mLT-â (BB.F6) | | Anti-mLT-α (AF.B3) | |
|---|---|---|---|---|
| | MFCI[b] | % Inh[c] | MFCI[b] | % Inh[c] |
| 0[a] | 6 | — | 6 | — |
| 0 | 85 | 0 | 85 | 0 |
| 0.01 | 71 | 18 | 84 | 2 |
| 0.03 | 67 | 23 | 86 | 0 |
| 0.1 | 51 | 44 | 86 | 0 |
| 0.3 | 36 | 62 | 84 | 2 |
| 1.0 | 29 | 71 | 89 | 0 |
| 3.0 | 17 | 86 | 88 | 0 |
| 10.0 | 11 | 94 | 95 | 0 |
| 30.0 | 10 | 95 | 94 | 0 |
| 100.0 | 8 | 98 | 92 | 0 |

[a]no receptor added
[b]Mean Fluorescence Channel No.
[c]Percent Inhibition

Example 8

LT-β-R Blocking Agents Inhibit Th1-Mediated Contact Hypersensitivity in Mouse 20 g female Balb/c mice (Jackson Laboratories, Bar Harbor, Me.) were initially sensitized by applying 25 μL of 0.5% 2,4-dinitrofluorobenzene (DNFB) in 4:1 v/v acetone:olive oil onto the bottom of each hind foot. Twenty-four hours after the initial sensitization, we again sensitized each mouse with 25 μl of the same solution. Sensitizations were performed while restraining the unanesthetized mouse. On day 5 (120 hours after the initial sensitization), we anesthetized the mice with 90:10 mg/kg ketamine:xylazine (i.p.) and applied a sub-irritant dose of 10 μl of 0.2% DNFB to the dorsal and ventral surfaces of the left ear. The right ear received a similar application of the 4:1 v/v acetone:olive oil vehicle.

Four hours after challenging the immune response, we administered increasing concentrations of the mLT-β-R-Fc (0.08-5.0 mg/kg; Example 2) to the mice in 0.1 ml of phosphate buffered saline (PBS) by intravenous injection. Injections of PBS buffer alone, or 20 mg/kg of a human IgG fusion protein (LFA3-Fc) (Miller et al., *J. Exp. Med.*, 178, pp. 211-22 (1993)) served as negative controls. Injection of 8 mg/kg of an anti-VLA4-specific mAb (PS/2 mAb; Chisolm et al., *Eur. J. Immunol.*, 23, pp. 682-88 (1993))—which is known to inhibit CHS by blocking the influx of T cells into the challenge site—served as a positive control. Groups of four to eight mice were treated per concentration of antibody.

Twenty four hours after challenge, mice were again anesthetized with ketamine:xylazine and the ear thickness of both ears measured with an engineer's micrometer to an accuracy of $10^{-4}$ inches. The ear swelling response for each mouse was the difference between its control- and DNFB-challenged ear thickness. Typical uninhibited ear swelling responses were $95$-$110 \times 10^{-4}$ inches. Inhibition of the ear swelling response was judged by comparison of treated groups with their negative control group. Statistical significance of the difference among treatment groups was evaluated using one-way analysis of variance followed by computation of the Tukey-Kramer Honestly Significant Difference (JMP, SAS Institute) using $p<0.05$.

FIG. 5 shows that administering increasing concentrations of mLT-β-R-Fc causes a significant reduction in the ear swelling response of DNFB-treated mice compared to uninhibited DNFB-treated control animals (PBS and LFA3-Fc). Soluble LT-β-R (from about 1-5 mg/kg) can block this contact DTH reaction as effectively as the inhibitor anti-VLA4-specific mAb. The portion of this ear swelling assay which is not inhibited probably results from "nonspecific" granulocyte infiltration.

Example 11

Dextran Sulphate Solution (DSS) IUD Model

Mice were treated as defined in the figure legend with hLFA3-Ig, i.e. a control Ig fusion protein or mLTβR-Ig by intraperitoneal injection. At day 0, the drinking water was changed to a 5% dextran sulphate solution and the mice were left Mice were treated as defined in the figure legend with hLFA3-Ig, i.e. a control Ig fusion protein or mLTR-Ig by intraperitoneal injection. At day 0, the drinking water was changed to a 5% dextran sulphate solution and the mice were left on this fluid for one week. One week later, i.e. 2 weeks after starting DSS administration, mice were sacrificed and the weight change and the large bowel length (from anus to cecum) measured. FIGS. 6 and 7 shows the weight changes and bowel lengths after various treatments. The shortened bowel length as well as the weight loss is indicative of TED. It was seen that mLTf3R-Ig treatment dramatically prevents the colon shortening and weight loss indicating efficacy.

FIG. 6:
The weight change observed 14 days post initiation of DSS in the drinking water following various treatments. Veh=vehicle, LTBr and LFA3 refer to mLTβR-Ig and hLFA3-Ig fusion proteins that were administered by intraperitoneal injection of 100 ug 1 week prior to adding DSS, at the point of DSS administration and 1 week later (i.e. 3 injections at $-1$, 0 and 1 week). There were 10 animals per group.

FIG. 7:
The colon length at 14 days post DSS administration following the various treatments described in 6.

Example 10

CD45RB$^{hi}$/scid Model of IBD

Figure 8:
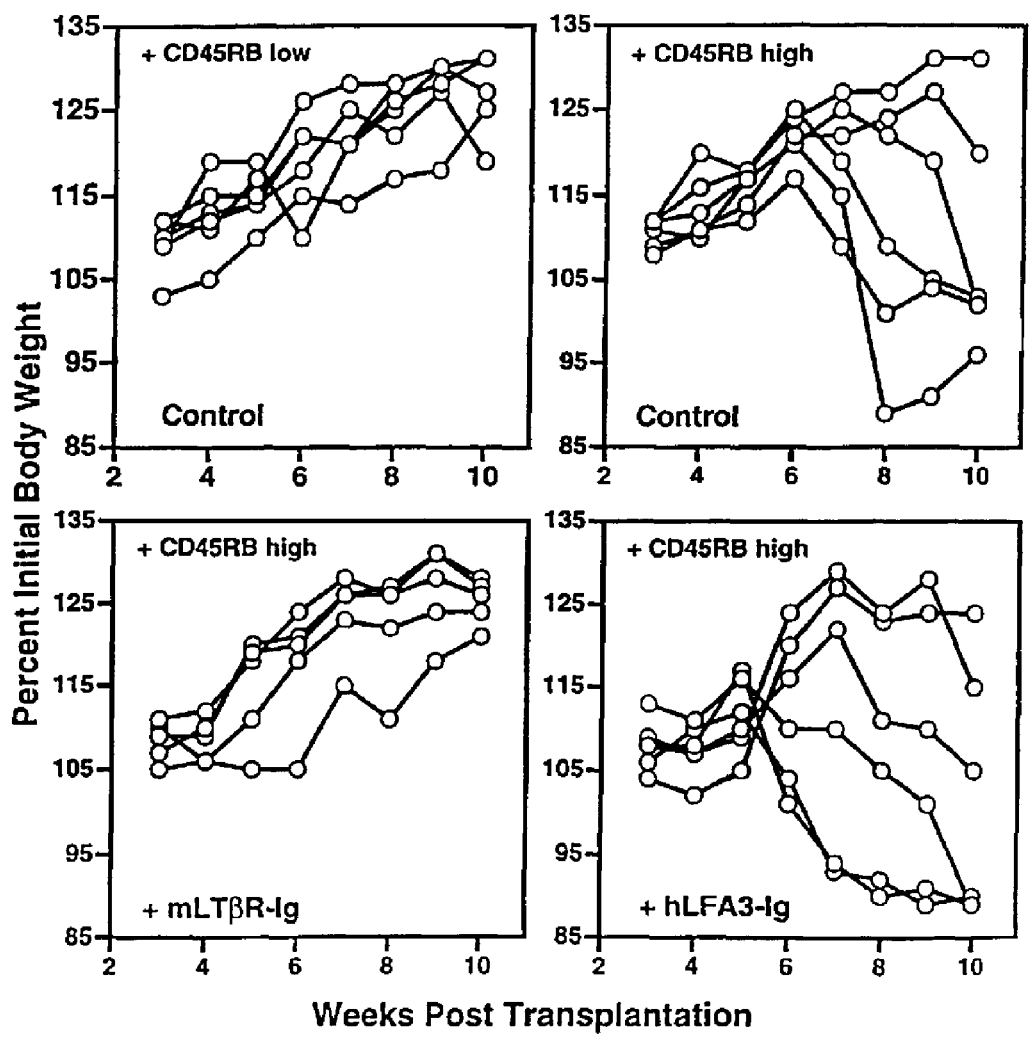
FIG. 8 is a time course of the body weight of mice following injection of $CD45RB^{low}CD4$ positive T cells; $CD45RB^{high}CD4$ positive T cells; $CD45RB^{high}$ and in LTβR-lg; and $CD45RB^{high}$ and hLFA3-lg.
Figure 9:
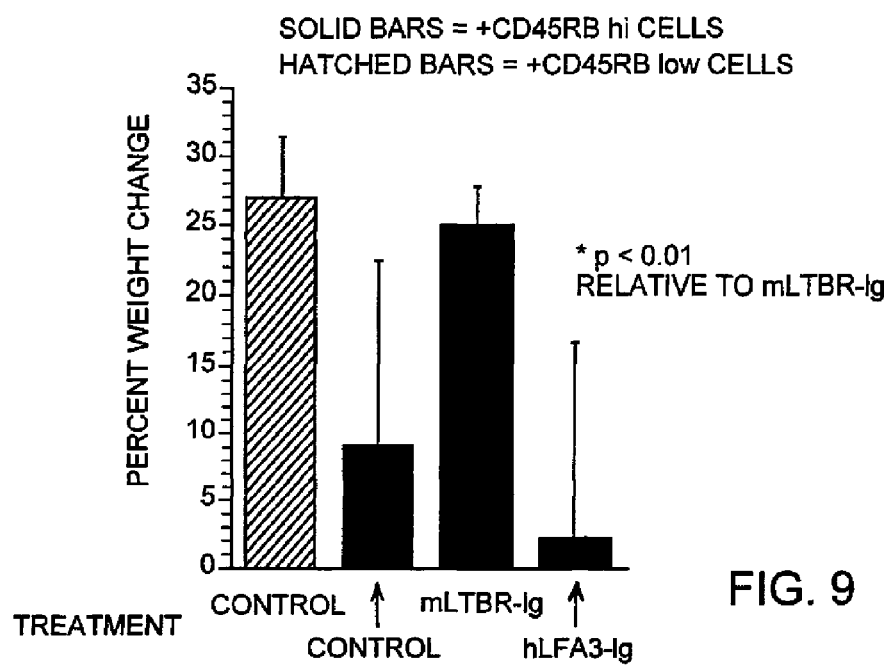
FIG. 9 is a graphical representation of the mean and standard deviations of the body weights observed following the treatments in FIGS. 8-11.

CD4 positive T cells are isolated from C.B-17 female mice using magnetic bead technology as described earlier (F. Powrie et al International immunology 5:1461-1471 1993). The CD4 cells depleted of CD8 positive T cells, B cells and monocytes were then sorted by fluorescence activated cell sorting into CD415RB$^{high}$ and CD45RB$^{low}$ populations also essentially as described above. $5 \times 10^5$ CD45RB cells were injected intravenously into female C.B-17 scid mice and the body weight of the mice was followed. It can be seen that animals reconstituted with CD45RB$^{low}$ cells gained weight in a normal manner. In contrast, animals receiving CD45RB$^{high}$ cells eventually lost weight and at 10 weeks were near death. When the control mice had lost roughly 20% of their starting weight, the mice were sacrificed and various organs analyzed by histology. Typically diseased animals looked cachectic, had diarrhea and had dramatically enlarged colons and ceca. Animals treated as described in the figure legend with hLFA3-Ig were similar to untreated animals, whereas animal treated with mLTβR-Ig had not undergone weight loss, had relatively normal sized colons and lacked the massive inflammatory infiltrates typically observed in the colon. FIG. 8 shows the time course of weight loss in CD45RB$^{high}$ injected animals treated in various ways and FIG. 9 shows the final body weights at 8 weeks post injection. The efficacy of mLTβR-Ig in two very different models of IBD, i.e. the CD45RB and DSS models, represents strong evidence for a profound effect of this treatment on the immune system.

FIG. 8:
Time course of the body weigh following injection of CD45RB CD4 positive T cells into scid mice. Each curve represents one animal and the inscriptions in the panels refer to which cells were injected i.e. CD45RB$^{high\ or\ low}$ and the nature of the treatment. Animal were treated weekly with 100 μg of protein injected intraperitoneally. Treatment started 2 weeks prior to the injection of the cells and continued throughout the course of the experiment.

FIG. 9:
Mean and standard deviations of the body weights observed following various treatments at 10 weeks post transplantation (5-6 animals per group).

Example 11

A SRBC Model of Delayed Type Hypersensitivity

Figure 10:
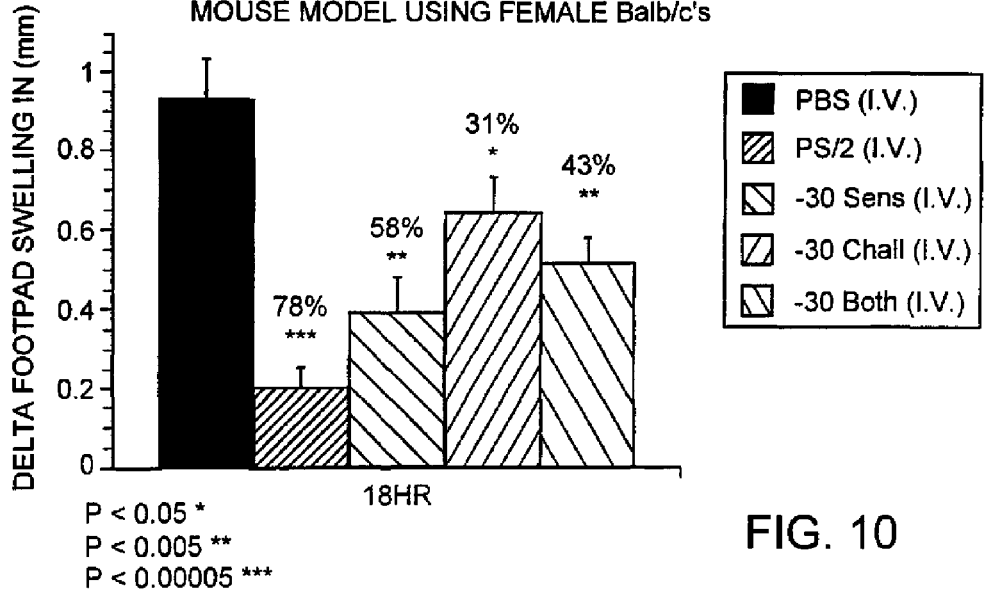
FIG. 10 is a representation of the increase in footpad thickness of mice injected with negative and positive controls and mLTβR-lg.

Female balb/c mice are sensitized by subcutaneous injection of $2 \times 10^7$ washed sheep red blood cells (SRBC) in PBS. After 5 days, mice are challenged with a injection of $1 \times 10^8$ SRBC in PBS into the right footpad (subplantar injection). Various times after injection into the footpad, the footpad thickness was measured with calipers. FIG. 10 shows the footpad swelling response in mice either treated by intraperitoneal injection with mLTβR-Ig. Treatment with mLTβR-Ig either at the point of sensitization or at both sensitization or challenge stages inhibited the SRBC induced DTH response.

FIG. 10:

Shown is the increase in footpad thickness measured 18 h post injection with SRBC challenge. Treatments were either a negative control injection of PBS, a positive control antibody PS/2 that blocks VLA4 interactions and hence cell trafficking and mLTβR-Ig (100 μg intravenous injections) given either immediately prior to the sensitizing subcutaneous injection of SRBC, at the challenge point or at both times.

selected from the amino acids of SEQ ID NO:1, wherein the functional sequence comprises the LT-β-R ligand binding domain.

5. The method of claim 1, wherein the animal is a human.

6. A method for inhibiting a Th1 cell-associated disorder in an animal comprising the step of administering a pharmaceutical composition which comprises an effective amount of a lymphotoxin-β receptor (LT-β-R) blocking agent and a pharmaceutically acceptable carrier, wherein the LT-β-R blocking agent is a composition comprising soluble LT-β-R.

7. The method according to claim 6, wherein the Th1 cell-associated disorder is Sjogren's syndrome.

8. The method of claim 6, wherein the soluble LT-β-R comprises one or more heterologous protein domains.

9. The method according to claim 8, wherein the one or more heterologous protein domains comprises a human immunoglobulin Fc domain.

10. The method according to claim 6, wherein the soluble LT-β-R comprises a functional sequence of amino acids selected from the amino acids of SEQ ID NO:1, wherein the functional sequence comprises the LT-β-R ligand binding domain.

---

---

What is claimed is:

1. A method for treating Sjogren's syndrome in an animal comprising the step of administering a pharmaceutical composition which comprises a therapeutically effective amount of a lymphotoxin-β receptor (LT-β-R) blocking agent and a pharmaceutically acceptable carrier, wherein the LT-β-R blocking agent is a composition comprising soluble LT-β-R.

2. The method of claim 1, wherein the soluble LT-β-R comprises one or more heterologous protein domains.

3. The method according to claim 2, wherein the one or more heterologous protein domains comprise a human immunoglobulin Fc domain.

4. The method according to claim 1, wherein the soluble LT-β-R comprises a functional sequence of amino acids 11. The method of claim 6, wherein the animal is a human.

12. A method for inhibiting Sjogren's syndrome in an animal comprising the step of administering a pharmaceutical composition which comprises an effective amount of a lymphotoxin-β receptor (LT-β-R) blocking agent and a pharmaceutically acceptable carrier, wherein the LT-β-R blocking agent is a composition comprising soluble LT-β-R.

13. The method of claim 12, wherein the soluble LT-β-R comprises one or more heterologous protein domains.

14. The method according to claim 13, wherein the one or more heterologous protein domains comprise a human immunoglobulin Fc domain.

15. The method according to claim 12, wherein the soluble LT-β-R comprises a functional sequence of amino acids selected from the amino acids of SEQ ID NO:1, wherein the functional sequence comprises the LT-β-R ligand binding domain.

16. The method of claim 12, wherein the animal is a human.

* * * * *

UNITED STATES PATENT AND TRADEMARK OFFICE
CERTIFICATE OF CORRECTION

PATENT NO. : 8,455,445 B2
APPLICATION NO. : 13/037092
DATED : June 4, 2013
INVENTOR(S) : Jeffrey L. Browning et al.

It is certified that error appears in the above-identified patent and that said Letters Patent is hereby corrected as shown below:

In the Specification:

At column 29, the paragraph at lines 46 through 61 should read:

Mice were treated as defined in the figure legend with hLFA3-Ig, i.e. a control Ig fusion protein or mLTβR-Ig by intraperitoneal injection. At day 0, the drinking water was changed to a 5% dextran sulphate solution and the mice were left on this fluid for one week. One week later, i.e. 2 weeks after starting DSS administration, mice were sacrificed and the weight change and the large bowel length (from anus to cecum) measured. FIGS. 6 and 7 shows the weight changes and bowel lengths after various treatments. The shortened bowel length as well as the weight loss in indicative of IBD. It was seen that mLTβR-Ig treatment dramatically prevents the colon shortening and weight loss indicating efficacy.

In the Claims:

At column 31, claim number 4, the claim should be listed as follows:

The method according to claim 1, wherein the soluble LT-β-R comprises a functional sequence of amino acids selected from the amino acids of SEQ ID NO:1, wherein the functional sequence comprises the LT-β-R ligand binding domain.

Signed and Sealed this
Twenty-first Day of October, 2014

Michelle K. Lee
*Deputy Director of the United States Patent and Trademark Office*

CERTIFICATE OF CORRECTION (continued)
U.S. Pat. No. 8,455,445 B2

Please add these Claims 5 and 6 as follows:

Claim 5

-- The method of claim 1, wherein the animal is a human. --

Claim 6

-- A method for inhibiting a Th1 cell-associated disorder in an animal comprising the step of administering a pharmaceutical composition which comprises an effective amount of a lymphotoxin-β receptor (LT-β-R) blocking agent and a pharmaceutically acceptable carrier, wherein the LT-β-R blocking agent is a composition comprising soluble LT-β-R. --

UNITED STATES PATENT AND TRADEMARK OFFICE
CERTIFICATE OF CORRECTION

PATENT NO. : 8,455,445 B2
APPLICATION NO. : 13/037092
DATED : June 4, 2013
INVENTOR(S) : Jeffrey L. Browning et al.

It is certified that error appears in the above-identified patent and that said Letters Patent is hereby corrected as shown below:

In the Specification:

At column 29, the paragraph at lines 46 through 61 should read:

Mice were treated as defined in the figure legend with hLFA3-Ig, i.e. a control Ig fusion protein or mLTβR-Ig by intraperitoneal injection. At day 0, the drinking water was changed to a 5% dextran sulphate solution and the mice were left on this fluid for one week. One week later, i.e. 2 weeks after starting DSS administration, mice were sacrificed and the weight change and the large bowel length (from anus to cecum) measured. FIGS. 6 and 7 shows the weight changes and bowel lengths after various treatments. The shortened bowel length as well as the weight loss in indicative of IBD. It was seen that mLTβR-Ig treatment dramatically prevents the colon shortening and weight loss indicating efficacy.

This certificate supersedes the Certificate of Correction issued October 21, 2014.

Signed and Sealed this
Eleventh Day of November, 2014

Michelle K. Lee
*Deputy Director of the United States Patent and Trademark Office*

CERTIFICATE OF CORRECTION (continued)

In the Claims:

At Column 31, line 66 - Column 32, line 55, claim number 4, the claim should be listed as follows:

The method according to claim 1, wherein the soluble LT-β-R comprises a functional sequence of amino acids selected from the amino acids of SEQ ID NO:1, wherein the functional sequence comprises the LT-β-R ligand binding domain.

At Column 32, line 56, please add these Claims 5 and 6 as follows:

Claim 5

-- The method of claim 1, wherein the animal is a human. --

Claim 6

-- A method for inhibiting a Th1 cell-associated disorder in an animal comprising the step of administering a pharmaceutical composition which comprises an effective amount of a lymphotoxin-β receptor (LT-β-R) blocking agent and a pharmaceutically acceptable carrier, wherein the LT-β-R blocking agent is a composition comprising soluble LT-β-R. --

SEQUENCE LISTING

<160> NUMBER OF SEQ ID NOS: 1

<210> SEQ ID NO 1
<211> LENGTH: 197
<212> TYPE: PRT
<213> ORGANISM: Homo sapiens

<400> SEQUENCE: 1

Ser Gln Pro Gln Ala Val Pro Pro Tyr Ala Ser Glu Asn Gln Thr Cys
 1               5                  10                  15

Arg Asp Gln Glu Lys Glu Tyr Tyr Glu Pro Gln His Arg Ile Cys Cys
             20                  25                  30

Ser Arg Cys Pro Pro Gly Thr Tyr Val Ser Ala Lys Cys Ser Arg Ile
         35                  40                  45

Arg Asp Thr Val Cys Ala Thr Cys Ala Glu Asn Ser Tyr Asn Glu His
     50                  55                  60

Trp Asn Tyr Leu Thr Ile Cys Gln Leu Cys Arg Pro Cys Asp Pro Val
 65                  70                  75                  80

Met Gly Leu Glu Glu Ile Ala Pro Cys Thr Ser Lys Arg Lys Thr Gln
                 85                  90                  95

Cys Arg Cys Gln Pro Gly Met Phe Cys Ala Ala Trp Ala Leu Glu Cys
            100                 105                 110

Thr His Cys Glu Leu Leu Ser Asp Cys Pro Pro Gly Thr Glu Ala Glu
        115                 120                 125

Leu Lys Asp Glu Val Gly Lys Gly Asn Asn His Cys Val Pro Cys Lys
    130                 135                 140

Ala Gly His Phe Gln Asn Thr Ser Ser Pro Ser Ala Arg Cys Gln Pro
145                 150                 155                 160

His Thr Arg Cys Glu Asn Gln Gly Leu Val Glu Ala Ala Pro Gly Thr
                165                 170                 175

Ala Gln Ser Asp Thr Thr Cys Lys Asn Pro Leu Glu Pro Leu Pro Pro
            180                 185                 190

Glu Met Ser Gly Thr
        195